United States Patent
Schechter et al.

(10) Patent No.: US 7,799,028 B2
(45) Date of Patent: *Sep. 21, 2010

(54) ARTICULATING BIPOLAR ELECTROSURGICAL INSTRUMENT

(75) Inventors: David A. Schechter, Longmont, CO (US); Stephen G. Solga, Longmont, CO (US); Duane E. Kerr, Berthoud, CO (US); Scott D. Nelson, Denver, CO (US); Mark R. Henault, Westminster, CO (US); Joseph D. Bucciaglia, Louisville, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 21 days.

This patent is subject to a terminal disclaimer.

(21) Appl. No.: 12/238,924

(22) Filed: Sep. 26, 2008

(65) Prior Publication Data
US 2009/0018535 A1    Jan. 15, 2009

Related U.S. Application Data

(63) Continuation of application No. 11/230,027, filed on Sep. 19, 2005, now Pat. No. 7,540,872.

(60) Provisional application No. 60/611,622, filed on Sep. 21, 2004.

(51) Int. Cl.
*A61B 18/14* (2006.01)
(52) U.S. Cl. .............................. 606/51; 606/41; 606/50; 606/52; 606/205
(58) Field of Classification Search ............. 606/32–52, 606/205–207
See application file for complete search history.

(56) References Cited

U.S. PATENT DOCUMENTS 371,664 A    10/1887    Brannan et al.

(Continued)

FOREIGN PATENT DOCUMENTS

CA    2104423    2/1994

(Continued)

OTHER PUBLICATIONS

Michael Choti, "Abdominoperineal Resection with the LigaSure Vessel Sealing System and LigaSure. Atlas 20 cm Open Instrument"; Innovations That Work, Jun. 2003.

(Continued)

*Primary Examiner*—Michael Peffley
*Assistant Examiner*—Ronald Hupczey, Jr.

(57) ABSTRACT

A bipolar electrosurgical instrument has a pair of pivotable juxtaposed jaw members and a locking mechanism operatively associated with a second of the jaw members. The locking mechanism has a first position engaged with the second jaw member for preventing movement of the second jaw member between an axially aligned orientation and at least one angled orientation, and a second position. The second position is disengaged from the second jaw member allowing for movement of the second jaw member between the axially aligned orientation and the at least one angled orientation. The instrument has an actuation mechanism operatively connected to a first of the jaw members with the actuation mechanism operable to move the first jaw member between an axially aligned first orientation and at least one angled orientation. An articulation knob is operatively associated with the locking mechanism and effectuates independent operation of the locking and actuation mechanisms.

15 Claims, 17 Drawing Sheets

U.S. PATENT DOCUMENTS

| | | |
|---|---|---|
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A * | 8/1988 | Jaeger ......................... 600/564 |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A * | 5/1993 | Knoepfler ..................... 606/16 |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A * | 2/1994 | Quadri ......................... 606/207 |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |

| | | | | | |
|---|---|---|---|---|---|
| 5,334,183 A | 8/1994 | Wuchinich | 5,531,744 A | 7/1996 | Nardella et al. |
| 5,334,215 A | 8/1994 | Chen | 5,536,251 A | 7/1996 | Evard et al. |
| 5,336,220 A | 8/1994 | Ryan et al. | 5,540,684 A | 7/1996 | Hassler, Jr. |
| 5,336,221 A | 8/1994 | Anderson | 5,540,685 A | 7/1996 | Parins et al. |
| 5,342,359 A | 8/1994 | Rydell | 5,540,706 A | 7/1996 | Aust et al. |
| 5,342,381 A | 8/1994 | Tidemand | 5,540,715 A | 7/1996 | Katsaros et al. |
| 5,342,393 A | 8/1994 | Stack | 5,542,945 A | 8/1996 | Fritzsch |
| 5,344,424 A | 9/1994 | Roberts et al. | 5,558,671 A | 9/1996 | Yates |
| 5,350,391 A | 9/1994 | Iacovelli | 5,558,672 A | 9/1996 | Edwards et al. |
| 5,352,222 A | 10/1994 | Rydell | 5,562,619 A | 10/1996 | Mirarchi et al. |
| 5,354,271 A | 10/1994 | Voda | 5,562,699 A | 10/1996 | Heimberger et al. |
| 5,356,408 A | 10/1994 | Rydell | 5,562,720 A | 10/1996 | Stern et al. |
| 5,366,477 A | 11/1994 | LeMarie, III et al. | 5,564,615 A | 10/1996 | Bishop et al. |
| 5,368,600 A | 11/1994 | Failla et al. | 5,569,241 A | 10/1996 | Edwardds |
| 5,374,277 A | 12/1994 | Hassler | 5,569,243 A | 10/1996 | Kortenbach et al. |
| 5,376,089 A | 12/1994 | Smith | 5,571,100 A | 11/1996 | Goble et al. |
| 5,383,875 A | 1/1995 | Bays et al. | 5,573,424 A | 11/1996 | Poppe |
| 5,383,897 A | 1/1995 | Wholey | 5,573,534 A | 11/1996 | Stone |
| 5,389,098 A | 2/1995 | Tsuruta et al. | 5,573,535 A | 11/1996 | Viklund |
| 5,389,103 A | 2/1995 | Melzer et al. | 5,575,799 A | 11/1996 | Bolanos et al. |
| 5,389,104 A | 2/1995 | Hahnen et al. | 5,575,805 A | 11/1996 | Li |
| 5,391,166 A | 2/1995 | Eggers | 5,578,052 A | 11/1996 | Koros et al. |
| 5,391,183 A | 2/1995 | Janzen et al. | 5,579,781 A | 12/1996 | Cooke |
| 5,396,900 A | 3/1995 | Slater et al. | 5,582,611 A | 12/1996 | Tsukagoshi et al. |
| 5,403,312 A | 4/1995 | Yates et al. | 5,582,617 A | 12/1996 | Klieman et al. |
| 5,403,342 A | 4/1995 | Tovey et al. | 5,585,896 A | 12/1996 | Yamazaki et al. |
| 5,405,344 A | 4/1995 | Williamson et al. | 5,590,570 A | 1/1997 | LeMaire, III et al. |
| 5,409,763 A | 4/1995 | Serizawa et al. | 5,591,181 A | 1/1997 | Stone et al. |
| 5,411,519 A | 5/1995 | Tovey et al. | 5,597,107 A | 1/1997 | Knodel et al. |
| 5,411,520 A | 5/1995 | Nash et al. | 5,601,224 A | 2/1997 | Bishop et al. |
| 5,413,571 A | 5/1995 | Katsaros et al. | 5,601,601 A | 2/1997 | Tal et al. |
| 5,415,656 A | 5/1995 | Tihon et al. | 5,601,641 A | 2/1997 | Stephens |
| 5,415,657 A | 5/1995 | Taymor-Luria | 5,603,711 A | 2/1997 | Parins et al. |
| 5,422,567 A | 6/1995 | Matsunaga | 5,603,723 A | 2/1997 | Aranyi et al. |
| 5,423,810 A | 6/1995 | Goble et al. | 5,611,798 A | 3/1997 | Eggers |
| 5,425,690 A | 6/1995 | Chang | 5,611,808 A | 3/1997 | Hossain et al. |
| 5,425,739 A | 6/1995 | Jessen | 5,611,813 A | 3/1997 | Lichtman |
| 5,429,616 A | 7/1995 | Schaffer | 5,620,415 A | 4/1997 | Lucey et al. |
| 5,431,672 A | 7/1995 | Cote et al. | 5,620,453 A | 4/1997 | Nallakrishnan |
| 5,431,674 A | 7/1995 | Basile et al. | 5,620,459 A | 4/1997 | Lichtman |
| 5,437,292 A | 8/1995 | Kipshidze et al. | 5,624,452 A | 4/1997 | Yates |
| 5,438,302 A | 8/1995 | Goble | 5,626,578 A | 5/1997 | Tihon |
| 5,439,478 A | 8/1995 | Palmer | 5,626,609 A | 5/1997 | Zvenyatsky et al. |
| 5,441,517 A | 8/1995 | Kensey et al. | 5,630,833 A | 5/1997 | Katsaros et al. |
| 5,443,463 A | 8/1995 | Stern et al. | 5,637,110 A | 6/1997 | Pennybacker et al. |
| 5,443,464 A | 8/1995 | Russell et al. | 5,638,003 A | 6/1997 | Hall |
| 5,443,480 A | 8/1995 | Jacobs et al. | 5,643,294 A | 7/1997 | Tovey et al. |
| 5,445,638 A | 8/1995 | Rydell et al. | 5,647,869 A | 7/1997 | Goble et al. |
| 5,445,658 A | 8/1995 | Durrfeld et al. | 5,647,871 A | 7/1997 | Levine et al. |
| 5,449,480 A | 9/1995 | Kuriya et al. | 5,649,959 A | 7/1997 | Hannam et al. |
| 5,451,224 A | 9/1995 | Goble et al. | 5,655,650 A | 8/1997 | Naitou |
| 5,454,823 A | 10/1995 | Richardson et al. | 5,658,281 A | 8/1997 | Heard |
| 5,454,827 A | 10/1995 | Aust et al. | D384,413 S | 9/1997 | Zlock et al. |
| 5,456,684 A * | 10/1995 | Schmidt et al. ............ 606/41 | 5,662,667 A | 9/1997 | Knodel |
| 5,458,598 A | 10/1995 | Feinberg et al. | 5,665,100 A | 9/1997 | Yoon |
| 5,460,629 A | 10/1995 | Shlain et al. | 5,667,526 A | 9/1997 | Levin |
| 5,461,765 A | 10/1995 | Linden et al. | 5,674,220 A | 10/1997 | Fox et al. |
| 5,462,546 A | 10/1995 | Rydell | 5,674,229 A | 10/1997 | Tovey et al. |
| 5,472,442 A | 12/1995 | Klicek | 5,681,282 A | 10/1997 | Eggers et al. |
| 5,472,443 A | 12/1995 | Cordis et al. | 5,688,270 A | 11/1997 | Yates et al. |
| 5,478,351 A | 12/1995 | Meade et al. | 5,690,652 A | 11/1997 | Wurster et al. |
| 5,480,409 A | 1/1996 | Riza | 5,690,653 A | 11/1997 | Richardson et al. |
| 5,484,436 A | 1/1996 | Eggers et al. | 5,693,051 A | 12/1997 | Schulze et al. |
| 5,496,312 A | 3/1996 | Klicek | 5,693,920 A | 12/1997 | Maeda |
| 5,496,317 A | 3/1996 | Goble et al. | 5,695,522 A | 12/1997 | LeMaire, III et al. |
| 5,496,347 A | 3/1996 | Hashiguchi et al. | 5,700,261 A | 12/1997 | Brinkerhoff |
| 5,499,997 A | 3/1996 | Sharpe et al. | 5,700,270 A | 12/1997 | Peyser et al. |
| 5,509,922 A | 4/1996 | Aranyi et al. | 5,702,390 A | 12/1997 | Austin et al. |
| 5,512,721 A | 4/1996 | Young et al. | 5,707,369 A | 1/1998 | Vaitekunas et al. |
| 5,514,134 A | 5/1996 | Rydell et al. | 5,709,680 A | 1/1998 | Yates et al. |
| 5,527,313 A | 6/1996 | Scott et al. | 5,716,366 A | 2/1998 | Yates |
| 5,528,833 A | 6/1996 | Sakuma | 5,720,744 A | 2/1998 | Eggleston et al. |
| 5,529,067 A | 6/1996 | Larsen et al. | 5,722,421 A | 3/1998 | Francese et al. |

| | | | | | |
|---|---|---|---|---|---|
| 5,725,536 A | 3/1998 | Oberlin et al. | 5,951,546 A | 9/1999 | Lorentzen |
| 5,727,428 A | 3/1998 | LeMaire, III et al. | 5,951,549 A | 9/1999 | Richardson et al. |
| 5,735,848 A | 4/1998 | Yates et al. | 5,954,720 A | 9/1999 | Wilson et al. |
| 5,743,906 A | 4/1998 | Parins et al. | 5,954,731 A | 9/1999 | Yoon |
| 5,752,973 A | 5/1998 | Kieturakis | 5,954,733 A | 9/1999 | Yoon |
| 5,755,717 A | 5/1998 | Yates et al. | 5,957,923 A | 9/1999 | Hahnen et al. |
| 5,759,188 A | 6/1998 | Yoon | 5,957,937 A | 9/1999 | Yoon |
| 5,766,130 A | 6/1998 | Selmonosky | 5,960,544 A | 10/1999 | Beyers |
| 5,766,166 A | 6/1998 | Hooven | 5,961,514 A | 10/1999 | Long et al. |
| 5,766,170 A | 6/1998 | Eggers | 5,964,758 A | 10/1999 | Dresden |
| 5,766,196 A | 6/1998 | Griffiths | 5,976,132 A | 11/1999 | Morris |
| 5,769,849 A | 6/1998 | Eggers | 5,984,932 A | 11/1999 | Yoon |
| 5,772,655 A | 6/1998 | Bauer et al. | 5,984,938 A | 11/1999 | Yoon |
| 5,772,670 A | 6/1998 | Brosa | 5,984,939 A | 11/1999 | Yoon |
| 5,776,128 A | 7/1998 | Eggers | 5,989,277 A | 11/1999 | LeMaire, III et al. |
| 5,776,130 A | 7/1998 | Buysse et al. | 5,993,466 A | 11/1999 | Yoon |
| 5,779,646 A | 7/1998 | Koblish et al. | 5,993,467 A | 11/1999 | Yoon |
| 5,779,701 A | 7/1998 | McBrayer et al. | 5,997,565 A | 12/1999 | Inoue |
| H1745 H | 8/1998 | Paraschac | 6,004,332 A | 12/1999 | Yoon et al. |
| 5,792,137 A | 8/1998 | Carr et al. | 6,004,335 A | 12/1999 | Vaitekunas et al. |
| 5,792,165 A | 8/1998 | Klieman et al. | 6,010,516 A | 1/2000 | Hulka et al. |
| 5,792,177 A | 8/1998 | Kaseda | 6,017,358 A | 1/2000 | Yoon et al. |
| 5,797,537 A | 8/1998 | Oberlin et al. | 6,021,693 A | 2/2000 | Feng-Sing |
| 5,797,927 A | 8/1998 | Yoon | 6,024,741 A | 2/2000 | Williamson et al. |
| 5,797,938 A * | 8/1998 | Paraschac et al. ............ 606/167 | 6,024,743 A | 2/2000 | Edwards |
| 5,797,941 A | 8/1998 | Schulze et al. | 6,024,744 A | 2/2000 | Kese et al. |
| 5,797,958 A | 8/1998 | Yoon | 6,027,522 A | 2/2000 | Palmer |
| 5,800,449 A | 9/1998 | Wales | 6,030,384 A | 2/2000 | Nezhat |
| 5,807,393 A | 9/1998 | Williamson, IV et al. | 6,033,399 A | 3/2000 | Gines |
| 5,810,764 A | 9/1998 | Eggers et al. | 6,039,733 A | 3/2000 | Buysse et al. |
| 5,810,805 A | 9/1998 | Sutcu et al. | 6,041,679 A | 3/2000 | Slater et al. |
| 5,810,808 A | 9/1998 | Eggers | 6,050,996 A | 4/2000 | Schmaltz et al. |
| 5,810,811 A | 9/1998 | Yates et al. | 6,053,914 A | 4/2000 | Eggers et al. |
| 5,810,877 A | 9/1998 | Roth et al. | 6,053,933 A | 4/2000 | Balazs et al. |
| 5,814,043 A | 9/1998 | Shapeton | D424,694 S | 5/2000 | Tetzlaff et al. |
| 5,814,054 A | 9/1998 | Kortenbach et al. | D425,201 S | 5/2000 | Tetzlaff et al. |
| 5,817,093 A | 10/1998 | Williamson, IV et al. | 6,059,782 A | 5/2000 | Novak et al. |
| 5,817,119 A * | 10/1998 | Klieman et al. ............ 606/174 | 6,066,139 A | 5/2000 | Ryan et al. |
| 5,820,630 A | 10/1998 | Lind | 6,074,386 A | 6/2000 | Goble et al. |
| 5,824,978 A | 10/1998 | Karasik et al. | 6,077,287 A | 6/2000 | Taylor et al. |
| 5,827,271 A | 10/1998 | Buysse et al. | 6,080,180 A | 6/2000 | Yoon et al. |
| 5,827,279 A | 10/1998 | Hughett et al. | RE36,795 E | 7/2000 | Rydell |
| 5,827,281 A | 10/1998 | Levin | 6,083,223 A | 7/2000 | Baker |
| 5,827,323 A * | 10/1998 | Klieman et al. ............ 606/205 | 6,086,586 A | 7/2000 | Hooven |
| 5,827,548 A | 10/1998 | Lavallee et al. | 6,086,601 A | 7/2000 | Yoon |
| 5,833,690 A | 11/1998 | Yates et al. | 6,090,107 A | 7/2000 | Borgmeier et al. |
| 5,843,080 A | 12/1998 | Fleenor et al. | 6,096,037 A | 8/2000 | Mulier et al. |
| 5,849,022 A | 12/1998 | Sakashita et al. | 6,099,550 A | 8/2000 | Yoon |
| 5,853,412 A | 12/1998 | Mayenberger | 6,102,909 A | 8/2000 | Chen et al. |
| 5,859,527 A | 1/1999 | Cook | 6,106,542 A | 8/2000 | Toybin et al. |
| 5,860,976 A | 1/1999 | Billings et al. | 6,110,171 A | 8/2000 | Rydell |
| 5,876,401 A | 3/1999 | Schulze et al. | 6,113,596 A | 9/2000 | Hooven et al. |
| 5,876,412 A | 3/1999 | Piraka | 6,113,598 A | 9/2000 | Baker |
| 5,882,567 A | 3/1999 | Cavallaro et al. | 6,117,158 A | 9/2000 | Measamer et al. |
| 5,891,141 A | 4/1999 | Rydell | 6,122,549 A | 9/2000 | Sharkey et al. |
| 5,891,142 A | 4/1999 | Eggers et al. | 6,123,701 A | 9/2000 | Nezhat |
| 5,893,863 A | 4/1999 | Yoon | H1904 H | 10/2000 | Yates et al. |
| 5,893,875 A | 4/1999 | O'Connor et al. | 6,126,658 A | 10/2000 | Baker |
| 5,893,877 A | 4/1999 | Gampp, Jr. et al. | 6,126,665 A | 10/2000 | Yoon |
| 5,897,563 A | 4/1999 | Yoon et al. | 6,139,563 A | 10/2000 | Cosgrove, III et al. |
| 5,902,301 A | 5/1999 | Olig | 6,143,005 A | 11/2000 | Yoon et al. |
| 5,906,630 A | 5/1999 | Anderhub et al. | 6,152,923 A | 11/2000 | Ryan |
| 5,908,420 A | 6/1999 | Parins et al. | 6,162,220 A | 12/2000 | Nezhat |
| 5,908,432 A | 6/1999 | Pan | 6,171,316 B1 | 1/2001 | Kovac et al. |
| 5,911,719 A | 6/1999 | Eggers | 6,174,309 B1 | 1/2001 | Wrublewski et al. |
| 5,913,874 A | 6/1999 | Berns et al. | 6,178,628 B1 | 1/2001 | Clemens et al. |
| 5,921,916 A | 7/1999 | Aeikens et al. | 6,179,834 B1 | 1/2001 | Buysse et al. |
| 5,921,984 A | 7/1999 | Sutcu et al. | 6,179,837 B1 | 1/2001 | Hooven |
| 5,925,043 A | 7/1999 | Kumar et al. | 6,183,467 B1 | 2/2001 | Shapeton et al. |
| 5,928,136 A | 7/1999 | Barry | 6,187,003 B1 | 2/2001 | Buysse et al. |
| 5,935,126 A | 8/1999 | Riza | 6,190,386 B1 | 2/2001 | Rydell |
| 5,941,869 A | 8/1999 | Patterson et al. | 6,190,400 B1 | 2/2001 | Vandemoer et al. |
| 5,944,718 A | 8/1999 | Dafforn et al. | 6,193,718 B1 | 2/2001 | Kortenbach et al. |

| Patent | Kind | Date | Inventor |
|---|---|---|---|
| 6,206,876 | B1 | 3/2001 | Levine et al. |
| 6,206,877 | B1 | 3/2001 | Kese et al. |
| 6,206,893 | B1 | 3/2001 | Klein et al. |
| 6,214,028 | B1 | 4/2001 | Yoon et al. |
| 6,217,602 | B1 | 4/2001 | Redmon |
| 6,217,615 | B1 | 4/2001 | Sioshansi et al. |
| 6,221,039 | B1 | 4/2001 | Durgin et al. |
| 6,223,100 | B1 | 4/2001 | Green |
| 6,224,593 | B1 | 5/2001 | Ryan et al. |
| 6,224,614 | B1 | 5/2001 | Yoon |
| 6,228,080 | B1 | 5/2001 | Gines |
| 6,228,083 | B1 | 5/2001 | Lands et al. |
| 6,248,124 | B1 | 6/2001 | Pedros et al. |
| 6,248,944 | B1 | 6/2001 | Ito |
| 6,261,307 | B1 | 7/2001 | Yoon et al. |
| 6,267,761 | B1 | 7/2001 | Ryan |
| 6,270,497 | B1 | 8/2001 | Sekino et al. |
| 6,270,508 | B1 | 8/2001 | Klieman et al. |
| 6,273,887 | B1 | 8/2001 | Yamauchi et al. |
| 6,277,117 | B1 | 8/2001 | Tetzlaff et al. |
| 6,280,458 | B1 | 8/2001 | Boche et al. |
| 6,283,961 | B1 | 9/2001 | Underwood et al. |
| D449,886 | S | 10/2001 | Tetzlaff et al. |
| 6,298,550 | B1 | 10/2001 | Kirwan |
| 6,302,424 | B1 | 10/2001 | Gisinger et al. |
| 6,319,262 | B1 | 11/2001 | Bates et al. |
| 6,319,451 | B1 | 11/2001 | Brune |
| 6,322,561 | B1 | 11/2001 | Eggers et al. |
| 6,322,580 | B1 | 11/2001 | Kanner |
| 6,325,795 | B1 | 12/2001 | Lindemann et al. |
| 6,334,860 | B1 | 1/2002 | Dorn |
| 6,334,861 | B1 | 1/2002 | Chandler et al. |
| 6,345,532 | B1 | 2/2002 | Coudray et al. |
| 6,350,264 | B1 | 2/2002 | Hooven |
| 6,352,536 | B1 | 3/2002 | Buysse et al. |
| 6,358,249 | B1 | 3/2002 | Chen et al. |
| 6,358,259 | B1 | 3/2002 | Swain et al. |
| 6,358,268 | B1 | 3/2002 | Hunt et al. |
| 6,364,879 | B1 | 4/2002 | Chen et al. |
| D457,958 | S | 5/2002 | Dycus et al. |
| D457,959 | S | 5/2002 | Tetzlaff et al. |
| 6,387,094 | B1 | 5/2002 | Eitenmuller |
| 6,391,035 | B1 | 5/2002 | Appleby et al. |
| 6,398,779 | B1 | 6/2002 | Buysse et al. |
| 6,402,747 | B1 | 6/2002 | Lindemann et al. |
| 6,409,728 | B1 | 6/2002 | Ehr et al. |
| H2037 | H | 7/2002 | Yates et al. |
| 6,419,675 | B1 | 7/2002 | Gallo, Sr. |
| 6,425,896 | B1 | 7/2002 | Baltschun et al. |
| 6,432,112 | B2 | 8/2002 | Brock et al. |
| 6,440,144 | B1 | 8/2002 | Bacher |
| 6,443,952 | B1 | 9/2002 | Mulier et al. |
| 6,443,970 | B1 | 9/2002 | Schulze et al. |
| 6,451,018 | B1 | 9/2002 | Lands et al. |
| 6,458,125 | B1 | 10/2002 | Cosmescu |
| 6,458,128 | B1 | 10/2002 | Schulze |
| 6,458,130 | B1 | 10/2002 | Frazier et al. |
| 6,461,352 | B2 | 10/2002 | Morgan et al. |
| 6,461,368 | B2 | 10/2002 | Fogarty et al. |
| 6,464,701 | B1 | 10/2002 | Hooven et al. |
| 6,464,702 | B2 | 10/2002 | Schulze et al. |
| 6,464,704 | B2 | 10/2002 | Schmaltz et al. |
| 6,485,489 | B2 | 11/2002 | Teirstein et al. |
| 6,494,888 | B1 | 12/2002 | Laufer et al. |
| 6,500,176 | B1 | 12/2002 | Truckai et al. |
| 6,506,196 | B1 | 1/2003 | Laufer |
| 6,508,815 | B1 | 1/2003 | Strul et al. |
| 6,511,480 | B1 | 1/2003 | Tetzlaff et al. |
| 6,514,215 | B1 | 2/2003 | Ouchi |
| 6,514,252 | B2 | 2/2003 | Nezhat et al. |
| 6,517,539 | B1 | 2/2003 | Smith et al. |
| 6,527,771 | B1 | 3/2003 | Weadock et al. |
| 6,533,784 | B2 | 3/2003 | Truckai et al. |
| 6,545,239 | B2 | 4/2003 | Spedale et al. |
| 6,558,385 | B1 | 5/2003 | McClurken et al. |
| 6,562,037 | B2 | 5/2003 | Paton et al. |
| 6,569,105 | B1 | 5/2003 | Kortenbach et al. |
| 6,582,450 | B2 | 6/2003 | Ouchi |
| 6,585,735 | B1 | 7/2003 | Frazier et al. |
| 6,602,252 | B2 | 8/2003 | Mollenauer |
| 6,605,790 | B2 | 8/2003 | Yoshida |
| 6,616,658 | B2 | 9/2003 | Ineson |
| 6,616,661 | B2 | 9/2003 | Wellman et al. |
| 6,620,161 | B2 | 9/2003 | Schulze et al. |
| 6,620,184 | B2 | 9/2003 | De Laforcade et al. |
| 6,626,901 | B1 | 9/2003 | Treat et al. |
| 6,638,287 | B2 | 10/2003 | Danitz et al. |
| 6,641,595 | B1 | 11/2003 | Moran et al. |
| 6,652,514 | B2 | 11/2003 | Ellman et al. |
| 6,652,521 | B2 | 11/2003 | Schulze |
| 6,656,175 | B2 | 12/2003 | Francischelli et al. |
| 6,656,177 | B2 | 12/2003 | Truckai et al. |
| 6,660,072 | B2 | 12/2003 | Chatterjee |
| 6,663,639 | B1 | 12/2003 | Laufer et al. |
| 6,663,641 | B1 | 12/2003 | Kovac et al. |
| 6,666,854 | B1 | 12/2003 | Lange |
| 6,669,696 | B2 | 12/2003 | Bacher et al. |
| 6,673,092 | B1 | 1/2004 | Bacher |
| 6,676,660 | B2 | 1/2004 | Wampler et al. |
| 6,676,676 | B2 | 1/2004 | Danitz et al. |
| 6,679,882 | B1 | 1/2004 | Kornerup |
| 6,682,527 | B2 | 1/2004 | Strul |
| 6,682,528 | B2 | 1/2004 | Frazier et al. |
| 6,685,724 | B1 | 2/2004 | Haluck |
| 6,689,131 | B2 | 2/2004 | McClurken |
| 6,692,445 | B2 | 2/2004 | Roberts et al. |
| 6,693,246 | B1 | 2/2004 | Rudolph et al. |
| 6,695,840 | B2 | 2/2004 | Schulze |
| 6,702,810 | B2 | 3/2004 | McClurken et al. |
| 6,723,092 | B2 | 4/2004 | Brown et al. |
| 6,726,068 | B2 | 4/2004 | Miller |
| 6,726,686 | B2 | 4/2004 | Buysse et al. |
| 6,726,694 | B2 | 4/2004 | Blatter et al. |
| 6,733,498 | B2 | 5/2004 | Paton et al. |
| 6,736,813 | B2 | 5/2004 | Yamauchi et al. |
| 6,743,229 | B2 | 6/2004 | Buysse et al. |
| 6,743,230 | B2 | 6/2004 | Lutze et al. |
| 6,743,239 | B1 | 6/2004 | Kuehn et al. |
| 6,755,843 | B2 | 6/2004 | Chung et al. |
| 6,756,553 | B1 | 6/2004 | Yamaguchi et al. |
| 6,757,977 | B2 | 7/2004 | Dambal et al. |
| D493,888 | S | 8/2004 | Reschke |
| 6,770,072 | B1 | 8/2004 | Truckai et al. |
| 6,773,409 | B2 | 8/2004 | Truckai et al. |
| 6,773,432 | B1 | 8/2004 | Clayman et al. |
| 6,773,434 | B2 | 8/2004 | Ciarrocca |
| 6,773,441 | B1 | 8/2004 | Laufer et al. |
| 6,775,575 | B2 | 8/2004 | Bommannan et al. |
| 6,776,780 | B2 | 8/2004 | Mulier et al. |
| 6,786,905 | B2 | 9/2004 | Swanson et al. |
| 6,790,217 | B2 | 9/2004 | Schulze et al. |
| 6,796,981 | B2 | 9/2004 | Wham et al. |
| D496,997 | S | 10/2004 | Dycus et al. |
| 6,800,825 | B1 | 10/2004 | Sasaki et al. |
| 6,802,843 | B2 | 10/2004 | Truckai et al. |
| 6,808,525 | B2 | 10/2004 | Latterell et al. |
| D499,181 | S | 11/2004 | Dycus et al. |
| 6,818,000 | B2 | 11/2004 | Muller et al. |
| 6,821,285 | B2 | 11/2004 | Laufer et al. |
| 6,835,200 | B2 | 12/2004 | Laufer et al. |
| 6,857,357 | B2 | 2/2005 | Fujii |
| 6,860,880 | B2 | 3/2005 | Treat et al. |
| 6,887,240 | B1 | 5/2005 | Lands et al. |
| 6,889,116 | B2 | 5/2005 | Jinno |
| 6,914,201 | B2 | 7/2005 | Van Vooren et al. |
| 6,926,716 | B2 | 8/2005 | Baker et al. |

| | | | | | | |
|---|---|---|---|---|---|---|
| 6,929,644 B2 | 8/2005 | Truckai et al. | | 7,232,440 B2 | 6/2007 | Dumbauld et al. |
| 6,932,810 B2 | 8/2005 | Ryan | | 7,241,288 B2 | 7/2007 | Braun |
| 6,932,816 B2 | 8/2005 | Phan | | 7,241,296 B2 | 7/2007 | Buysse et al. |
| 6,934,134 B2 | 8/2005 | Mori et al. | | 7,244,257 B2 | 7/2007 | Podjahsky et al. |
| 6,936,061 B2 | 8/2005 | Sasaki | | 7,246,734 B2 | 7/2007 | Shelto, IV |
| D509,297 S | 9/2005 | Wells | | 7,248,944 B2 | 7/2007 | Green |
| 6,942,662 B2 | 9/2005 | Goble et al. | | 7,252,667 B2 | 8/2007 | Moses et al. |
| 6,943,311 B2 | 9/2005 | Miyako | | 7,255,697 B2 | 8/2007 | Dycus et al. |
| 6,953,430 B2 | 10/2005 | Kidooka | | 7,267,677 B2 | 9/2007 | Johnson et al. |
| 6,953,461 B2 | 10/2005 | McClurken et al. | | 7,270,660 B2 | 9/2007 | Ryan |
| 6,958,070 B2 | 10/2005 | Witt et al. | | 7,270,664 B2 | 9/2007 | Johnson et al. |
| 6,960,210 B2 | 11/2005 | Lands et al. | | 7,276,068 B2 | 10/2007 | Johnson et al. |
| 6,964,662 B2 | 11/2005 | Kidooka | | 7,300,435 B2 | 11/2007 | Wham et al. |
| 6,966,907 B2 | 11/2005 | Goble | | 7,303,557 B2 | 12/2007 | Wham et al. |
| 6,972,017 B2 | 12/2005 | Smith et al. | | 7,311,709 B2 | 12/2007 | Truckai et al. |
| 6,977,495 B2 | 12/2005 | Donofrio | | 7,314,471 B2 | 1/2008 | Holman |
| 6,979,786 B2 | 12/2005 | Aukland et al. | | 7,318,823 B2 | 1/2008 | Sharps et al. |
| 6,981,628 B2 | 1/2006 | Wales | | 7,329,256 B2 | 2/2008 | Johnson et al. |
| 6,987,244 B2 | 1/2006 | Bauer | | 7,329,257 B2 | 2/2008 | Kanehira et al. |
| 6,994,707 B2 | 2/2006 | Ellman et al. | | D564,662 S | 3/2008 | Moses et al. |
| 6,994,709 B2 | 2/2006 | Iida | | 7,338,526 B2 | 3/2008 | Steinberg |
| 6,997,931 B2 | 2/2006 | Sauer et al. | | 7,342,754 B2 | 3/2008 | Fitzgerald et al. |
| 7,001,381 B2 | 2/2006 | Harano et al. | | 7,344,268 B2 | 3/2008 | Jhigamian |
| 7,011,657 B2 | 3/2006 | Truckai et al. | | D567,943 S | 4/2008 | Moses et al. |
| 7,033,354 B2 | 4/2006 | Keppel | | 7,367,976 B2 | 5/2008 | Lawes et al. |
| 7,033,356 B2 | 4/2006 | Latterell et al. | | 7,377,920 B2 | 5/2008 | Buysse et al. |
| 7,041,102 B2 | 5/2006 | Truckai et al. | | 7,384,420 B2 | 6/2008 | Dycus et al. |
| 7,044,948 B2 | 5/2006 | Keppel | | 7,384,421 B2 | 6/2008 | Hushka |
| 7,052,489 B2 | 5/2006 | Griego et al. | | 7,396,336 B2 | 7/2008 | Orszulak et al. |
| 7,052,496 B2 | 5/2006 | Yamauchi | | D575,395 S | 8/2008 | Hushka |
| 7,063,715 B2 | 6/2006 | Onuki et al. | | D575,401 S | 8/2008 | Hixson et al. |
| D525,361 S | 7/2006 | Hushka | | 7,435,249 B2 | 10/2008 | Buysse et al. |
| 7,070,597 B2 | 7/2006 | Truckai et al. | | 7,442,193 B2 | 10/2008 | Shields et al. |
| 7,083,618 B2 | 8/2006 | Couture et al. | | 7,442,194 B2 | 10/2008 | Dumbauld et al. |
| 7,083,619 B2 | 8/2006 | Truckai et al. | | 7,445,621 B2 | 11/2008 | Dumbauld et al. |
| 7,083,620 B2 * | 8/2006 | Jahns et al. .................. 606/51 | | 7,458,972 B2 | 12/2008 | Keppel |
| 7,087,051 B2 | 8/2006 | Bourne et al. | | 7,473,253 B2 | 1/2009 | Dycus et al. |
| 7,087,054 B2 | 8/2006 | Truckai et al. | | 7,481,810 B2 | 1/2009 | Dumbauld et al. |
| 7,090,673 B2 | 8/2006 | Dycus et al. | | 7,487,780 B2 | 2/2009 | Hooven |
| 7,090,689 B2 | 8/2006 | Nagase et al. | | 7,491,201 B2 | 2/2009 | Shields et al. |
| 7,101,371 B2 | 9/2006 | Dycus et al. | | 7,491,202 B2 | 2/2009 | Odom et al. |
| 7,101,372 B2 | 9/2006 | Dycus et al. | | 7,500,975 B2 | 3/2009 | Cunningham et al. |
| 7,101,373 B2 | 9/2006 | Dycus et al. | | 7,510,556 B2 | 3/2009 | Nguyen et al. |
| 7,103,947 B2 | 9/2006 | Sartor et al. | | 7,513,898 B2 | 4/2009 | Johnson et al. |
| 7,107,124 B2 | 9/2006 | Green | | 7,540,872 B2 * | 6/2009 | Schechter et al. ............. 606/50 |
| 7,112,199 B2 | 9/2006 | Cosmescu | | 7,549,995 B2 | 6/2009 | Schultz |
| D531,311 S | 10/2006 | Guerra et al. | | 7,553,312 B2 | 6/2009 | Tetzlaff et al. |
| 7,115,123 B2 | 10/2006 | Knowlton et al. | | 2002/0013583 A1 | 1/2002 | Camran et al. |
| 7,118,570 B2 | 10/2006 | Tetzlaff et al. | | 2002/0049442 A1 | 4/2002 | Roberts et al. |
| 7,118,587 B2 | 10/2006 | Dycus et al. | | 2002/0099372 A1 | 7/2002 | Schulze et al. |
| 7,131,860 B2 | 11/2006 | Sartor et al. | | 2002/0107517 A1 | 8/2002 | Witt et al. |
| 7,131,970 B2 | 11/2006 | Moses et al. | | 2002/0111624 A1 | 8/2002 | Witt et al. |
| 7,131,971 B2 | 11/2006 | Dycus et al. | | 2002/0188294 A1 | 12/2002 | Couture et al. |
| 7,135,020 B2 | 11/2006 | Lawes et al. | | 2003/0014052 A1 | 1/2003 | Buysse et al. |
| D533,942 S | 12/2006 | Kerr et al. | | 2003/0014053 A1 | 1/2003 | Nguyen et al. |
| 7,145,757 B2 | 12/2006 | Shea et al. | | 2003/0018331 A1 | 1/2003 | Dycus et al. |
| 7,147,638 B2 | 12/2006 | Chapman et al. | | 2003/0018332 A1 | 1/2003 | Schmaltz et al. |
| 7,150,097 B2 | 12/2006 | Sremcich et al. | | 2003/0032956 A1 | 2/2003 | Lands et al. |
| 7,150,749 B2 | 12/2006 | Dycus et al. | | 2003/0069570 A1 | 4/2003 | Witzel et al. |
| 7,153,314 B2 | 12/2006 | Laufer et al. | | 2003/0069571 A1 | 4/2003 | Treat et al. |
| D535,027 S | 1/2007 | James et al. | | 2003/0078578 A1 | 4/2003 | Truckai et al. |
| 7,156,842 B2 | 1/2007 | Sartor et al. | | 2003/0109875 A1 | 6/2003 | Tetzlaff et al. |
| 7,156,846 B2 | 1/2007 | Dycus et al. | | 2003/0114851 A1 | 6/2003 | Truckai et al. |
| 7,160,298 B2 | 1/2007 | Lawes et al. | | 2003/0139741 A1 | 7/2003 | Goble et al. |
| 7,160,299 B2 | 1/2007 | Baily | | 2003/0139742 A1 | 7/2003 | Wampler et al. |
| 7,169,146 B2 | 1/2007 | Truckai et al. | | 2003/0158548 A1 | 8/2003 | Phan et al. |
| 7,179,255 B2 | 2/2007 | Lettice et al. | | 2003/0158549 A1 | 8/2003 | Swanson |
| 7,179,258 B2 | 2/2007 | Buysse et al. | | 2003/0171747 A1 | 9/2003 | Kanehira et al. |
| 7,195,631 B2 | 3/2007 | Dumbauld | | 2003/0181910 A1 | 9/2003 | Dycus et al. |
| D541,418 S | 4/2007 | Schechter et al. | | 2003/0216732 A1 | 11/2003 | Truckai et al. |
| 7,207,990 B2 | 4/2007 | Lands et al. | | 2003/0220637 A1 | 11/2003 | Truckai et al. |
| D541,938 S | 5/2007 | Kerr et al | | 2003/0229344 A1 | 12/2003 | Dycus et al. |
| 7,223,265 B2 | 5/2007 | Keppel | | 2003/0236325 A1 | 12/2003 | Bonora |

| | | |
|---|---|---|
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0143263 A1 | 7/2004 | Schechter et al. |
| 2004/0148035 A1 | 7/2004 | Barrett et al. |
| 2004/0162557 A1 | 8/2004 | Tetzlaff et al. |
| 2004/0193153 A1 | 9/2004 | Sarter et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0004569 A1 | 1/2005 | Witt et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182327 A1 | 7/2009 | Unger |

| | | | | | | |
|---|---|---|---|---|---|---|
| 2009/0187188 | A1 | 7/2009 | Guerra et al. | GB | 2214430 A | 6/1989 |
| | | | | GB | 2213416 A | 8/1989 |
| | FOREIGN PATENT DOCUMENTS | | | JP | 61-501068 | 9/1984 |
| | | | | JP | 65-502328 | 3/1992 |
| DE | 2415263 | 10/1975 | | JP | 5-5106 | 1/1993 |
| DE | 2514501 | 10/1976 | | JP | 5-40112 | 2/1993 |
| DE | 2627679 | 1/1977 | | JP | 06343644 A2 | 12/1994 |
| DE | 3612646 | 4/1987 | | JP | 07265328 A2 | 10/1995 |
| DE | 8712328 | 3/1988 | | JP | 08056955 A2 | 3/1996 |
| DE | 4303882 | 8/1994 | | JP | 08252263 A2 | 10/1996 |
| DE | 4403252 | 8/1995 | | JP | 09010223 A2 | 1/1997 |
| DE | 19515914 | 7/1996 | | JP | 11244298 A2 | 9/1999 |
| DE | 29616210 | 1/1997 | | JP | 2000-342599 A2 | 12/2000 |
| DE | 19608716 | 4/1997 | | JP | 2000-350732 A2 | 12/2000 |
| DE | 19751106 | 5/1998 | | JP | 2001-008944 A2 | 1/2001 |
| DE | 19751108 | 5/1999 | | JP | 2001-029356 A2 | 2/2001 |
| DE | 19738457 | 1/2009 | | JP | 2001-128990 A2 | 5/2001 |
| EP | 0364216 | 4/1990 | | SU | 401367 | 11/1974 |
| EP | 0467501 | 1/1992 | | WO | WO 89/00757 | 1/1989 |
| EP | 0518230 | 12/1992 | | WO | WO 92/04873 | 4/1992 |
| EP | 0541930 | 5/1993 | | WO | WO 92/06642 | 4/1992 |
| EP | 0572131 | 12/1993 | | WO | WO 93/21845 | 11/1993 |
| EP | 0584787 | 3/1994 | | WO | WO 94/08524 | 4/1994 |
| EP | 0589453 | 3/1994 | | WO | WO 94/20025 | 9/1994 |
| EP | 0589555 | 3/1994 | | WO | WO 95/02369 | 1/1995 |
| EP | 0623316 | 11/1994 | | WO | WO 95/07662 | 3/1995 |
| EP | 0624348 | 11/1994 | | WO | WO 95/15124 | 6/1995 |
| EP | 0650701 | 5/1995 | | WO | WO 96/05776 | 2/1996 |
| EP | 0694290 | 3/1996 | | WO | WO 96/22056 | 7/1996 |
| EP | 0717966 | 6/1996 | | WO | WO 96/13218 | 9/1996 |
| EP | 0754437 | 3/1997 | | WO | WO 97/00646 | 1/1997 |
| EP | 0517243 | 9/1997 | | WO | WO 97/00647 | 1/1997 |
| EP | 0853922 | 7/1998 | | WO | WO 97/10764 | 3/1997 |
| EP | 0875209 | 11/1998 | | WO | WO 97/24073 | 7/1997 |
| EP | 0878169 | 11/1998 | | WO | WO 97/24993 | 7/1997 |
| EP | 0887046 | 1/1999 | | WO | WO 98/27880 | 7/1998 |
| EP | 0923907 | 6/1999 | | WO | WO 99/03407 | 1/1999 |
| EP | 0986990 | 3/2000 | | WO | WO 99/03408 | 1/1999 |
| EP | 1034747 | 9/2000 | | WO | WO 99/03409 | 1/1999 |
| EP | 1034748 | 9/2000 | | WO | WO 99/12488 | 3/1999 |
| EP | 1025807 | 10/2000 | | WO | WO 99/23933 | 5/1999 |
| EP | 1034746 | 10/2000 | | WO | WO 99/40857 | 8/1999 |
| EP | 1050278 | 11/2000 | | WO | WO 99/40861 | 8/1999 |
| EP | 1053719 | 11/2000 | | WO | WO 99/51158 | 10/1999 |
| EP | 1053720 | 11/2000 | | WO | WO 99/66850 | 12/1999 |
| EP | 1055399 | 11/2000 | | WO | WO 00/24330 | 5/2000 |
| EP | 1055400 | 11/2000 | | WO | WO 00/24331 | 5/2000 |
| EP | 1080694 | 3/2001 | | WO | WO 00/36986 | 6/2000 |
| EP | 1082944 | 3/2001 | | WO | WO 00/41638 | 7/2000 |
| EP | 1159926 | 12/2001 | | WO | WO 00/47124 | 8/2000 |
| EP | 1177771 | 2/2002 | | WO | WO 00/53112 | 9/2000 |
| EP | 1301135 | 4/2003 | | WO | WO 01/17448 | 3/2001 |
| EP | 1330991 | 7/2003 | | WO | WO 01/54604 | 8/2001 |
| EP | 1486177 | 6/2004 | | WO | WO 02/07627 | 1/2002 |
| EP | 1472984 | 11/2004 | | WO | WO 02/067798 | 9/2002 |
| EP | 0774232 | 1/2005 | | WO | WO 02/080783 | 10/2002 |
| EP | 1527747 | 5/2005 | | WO | WO 02/080784 | 10/2002 |
| EP | 1530952 | 5/2005 | | WO | WO 02/080785 | 10/2002 |
| EP | 1532932 | 5/2005 | | WO | WO 02/080786 | 10/2002 |
| EP | 1535581 | 6/2005 | | WO | WO 02/080793 | 10/2002 |
| EP | 1609430 | 12/2005 | | WO | WO 02/080794 | 10/2002 |
| EP | 1632192 | 3/2006 | | WO | WO 02/080795 | 10/2002 |
| EP | 1642543 | 4/2006 | | WO | WO 02/080796 | 10/2002 |
| EP | 1645238 | 4/2006 | | WO | WO 02/080797 | 10/2002 |
| EP | 1645240 | 4/2006 | | WO | WO 02/080798 | 10/2002 |
| EP | 1649821 | 4/2006 | | WO | WO 02/080799 | 10/2002 |
| EP | 1707143 | 10/2006 | | WO | WO 02/081170 | 10/2002 |
| EP | 1769765 | 4/2007 | | WO | WO 03/061500 | 7/2003 |
| EP | 1769766 | 4/2007 | | WO | WO 03/090630 | 11/2003 |
| EP | 1929970 | 6/2008 | | WO | WO 03/101311 | 12/2003 |
| EP | 1683496 | 12/2008 | | WO | WO 2004/032776 | 4/2004 |
| GB | 623316 | 5/1949 | | WO | WO 2004/032777 | 4/2004 |
| GB | 1490585 | 11/1977 | | WO | WO 2004/052221 | 6/2004 |

| | | |
|---|---|---|
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With The LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778 dated Oct. 31, 2000.
Int'l Search Report EP 98957771 dated Aug. 9, 2001.
Int'l Search Report EP 98958575.7 dated Sep. 20, 2002.
Int'l Search Report EP 04013772 dated Apr. 1, 2005.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05019429.9 dated May 6, 2008.
Int'l Search Report EP 05020665.5 dated Feb. 16, 2006.
Int'l Search Report EP 05020666.3 dated Feb. 17, 2006.
Int'l Search Report EP 05021197.8 dated Jan. 31, 2006.
Int'l Search Report EP 05021779.3 dated Jan. 18, 2006.
Int'l Search Report EP 05021780.1 dated Feb. 9, 2006.
Int'l Search Report EP 05021937.7 dated Jan. 13, 2006.

Int'l Search Report—extended—EP 05021937.7 dated Mar. 6, 2006.
Int'l Search Report EP 05023017.6 dated Feb. 16, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008515.6 dated Jan. 8, 2009.
Int'l Search Report EP 06008779.8 dated Jun. 13, 2006.
Int'l Search Report EP 06014461.5 dated Oct. 20, 2006.
Int'l Search Report EP 06020574.7 dated Sep. 21, 2007.
Int'l Search Report EP 06020583.8 dated Jan. 30, 2007.
Int'l Search Report EP 06020584.6 dated Jan. 12, 2007.
Int'l Search Report EP 06020756.0 dated Feb. 5, 2007.
Int'l Search Report EP 06 024122.1 dated Mar. 19, 2007.
Int'l Search Report EP 06024123.9 dated Feb. 26, 2007.
Int'l Search Report EP 07 001480.8 dated Apr. 12, 2007.
Int'l Search Report EP 07 001488.1 dated May 29, 2007.
Int'l Search Report EP 07 009026.1 dated Sep. 12, 2007.
Int'l Search Report Extended—EP 07 009029.5 dated Jul. 12, 2007.
Int'l Search Report EP 07 009321.6 dated Aug. 17, 2007.
Int'l Search Report EP 07 010672.9 dated Oct. 1, 2007.
Int'l Search Report EP 07 013779.9 dated Oct. 18, 2007.
Int'l Search Report EP 07 014016 dated Jan. 28, 2008.
Int'l Search Report EP 07 015191.5 dated Dec. 19, 2007.
Int'l Search Report EP 07 015601.3 dated Dec. 6, 2007.
Int'l Search Report EP 07 020283.3 dated Jan. 16, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report PCT/US98/18640 dated Dec. 17, 1998.
Int'l Search Report PCT/US98/23950 dated Dec. 29, 1998.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US03/28534 dated Dec. 19, 2003.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report EP 09 152267.2 Dated Jun. 15, 2009.
Int'l Search Report EP 09 152898.4 Dated Jun. 10, 2009.
Int'l Search Report PCT/US09/032690 dated Jun. 16, 2009.

* cited by examiner

ARTICULATING BIPOLAR ELECTROSURGICAL INSTRUMENT

CROSS REFERENCE TO RELATED PATENT APPLICATIONS

The present application is a Continuation of U.S. patent application Ser. No. 11/230,027, now U.S. Pat. No. 7,540,872, filed on Sep. 19, 2005, which claims priority to U.S. Provisional Patent Application Ser. No. 60/611,622, filed on Sep. 21, 2004, the entire content of each of these applications being incorporated herein by reference.

BACKGROUND

1. Technical Field

The present disclosure relates to electrosurgical instruments and, more particularly, to bipolar electro-surgical instruments having an articulating linkage for operating and/or effectuating movement of an end effector thereof.

2. Background of Related Art

Surgical procedures of the lungs currently employ Video Assisted Thoroscopic Surgical (VATS) techniques wherein an endoscopic surgical stapler is used to perform wedge resections, lobotomies, segmental resections, wedge biopsies or lung volume reduction surgeries.

Typically, the endoscopic surgical stapler can only be activated once per insertion into the thoracic cavity. For most surgical procedures involving the lungs, a single activation of the endoscopic surgical stapler cannot ligate and/or bisect all of the required areas for the given surgical procedure.

Accordingly, if multiple activations of the endoscopic surgical stapler are required to fully complete the surgical procedure, it is necessary to remove the endoscopic surgical stapler from the thoracic cavity after each fire; fit the endoscopic surgical stapler with a new, fully loaded staple cartridge, and reinsert the endoscopic surgical stapler into the thoracic cavity for the next activation thereof.

There is, therefore, a need for a surgical instrument that can be activated repetitively, as many times as the surgical procedure requires or as many times as necessary, without having to remove the surgical instrument from the thoracic cavity.

SUMMARY

According to an aspect of the present disclosure, a bipolar electrosurgical instrument is provided. The instrument includes a housing; a handle assembly operatively associated with the housing; a shaft extending from the housing, the shaft defining a longitudinal axis; and an end effector operatively associated with a distal end of the shaft. The end effector includes a first jaw member pivotably coupled to the distal end of the shaft; and a second jaw member pivotably coupled to the distal end of the shaft and in juxtaposed relation to the first jaw member. The first and second jaw members are movable from a first orientation in which the first and the second jaw member are axially aligned with the longitudinal axis and a plurality of second orientations in which the first and second jaw members are angled with respect to the longitudinal axis. The first and second jaw members have an open condition in which the first and second jaws members are spaced from one another and a closed condition in which the first and second jaw members are substantially in close proximity to one another. The second jaw member includes a plurality of inter-engagement elements.

The instrument further includes a locking mechanism operatively associated with the second jaw member. The locking mechanism has a first position in which the locking mechanism engages the second jaw member and prevents movement of the second jaw member between the first orientation and any of the plurality of second orientations, and a second position in which the locking mechanism is disengaged from the second jaw member and allows for movement of the second jaw member between the first orientation and any of the plurality of second orientations.

The instrument further includes an actuation mechanism operatively connected to the first jaw member. The actuation mechanism is operable to move the first jaw member between the first orientation and the plurality of second orientations.

The locking mechanism may include a locking shaft extending longitudinally through the shaft, wherein the locking shaft has a distal end operatively associated with the second jaw member; and a locking pin extending transversely from the distal end of the locking shaft, wherein the locking pin is selectively engagable with each of the plurality of inter-engagement elements of the second jaw member. Accordingly, when the locking mechanism is in the first position, the locking pin is engaged with the inter-engagement elements of the second jaw member. Additionally, when the locking mechanism is in the second position, the locking pin is disengaged from the inter-engaging elements of the second jaw member.

The actuation mechanism may include an actuation shaft reciprocally and rotatably disposed in the locking shaft, wherein the actuation shaft includes a distal end and a proximal end. The actuation mechanism may further include a band having a proximal end operatively connected to the distal end of the actuation shaft, and a distal end extending through an aperture formed in the distal end of the locking shaft and operatively connected to the first jaw member. Accordingly, when the actuation shaft is displaced in one of an axially proximal and distal direction, the first jaw member is articulated between the first orientation and the plurality of second orientations.

The instrument may further include an articulation knob operatively associated with the locking mechanism and the actuation mechanism. The articulation knob may effectuate independent operation of one of the locking mechanism and the actuation mechanism. It is envisioned that axial displacement of the articulation knob in one of a proximal and distal direction may manipulate the locking mechanism between the first and the second positions. It is further envisioned that rotation of the articulation knob may manipulate the actuation mechanism to move the first jaw member between the first orientation and the plurality of second orientations.

The locking mechanism may include a first collar operatively connected to a proximal end of the locking shaft; a pair of diametrically opposed connecting rods extending proximally from the first collar; and a second collar operatively connected to the proximal end of at least one of the connecting rods. The second collar may be rotatably supported on the articulation knob. Accordingly, as the articulation knob is axially displaced in one of the proximal and distal directions, the connecting rods transmit the axial displacement of the articulation knob to the locking rod.

The actuation mechanism may further include a lead screw operatively connected to a proximal end of the actuation shaft; and a drive shaft operatively interconnecting the lead screw and the articulation knob. Accordingly, rotation of the articulation knob moves the drive shaft and the drive shaft transmits rotation to the lead screw. Additionally, the lead screw axially displaces the actuation shaft.

The electrosurgical instrument may further include an indexing plate operatively associated with at least one of the connecting rods. The indexing plate may be operatively engagable with the articulation knob. The indexing plate defines a plurality of angular orientations for the second jaw member.

The second jaw member may be biased to the axially aligned orientation.

The end effector may further include a pivot pin extending through the first and the second jaw members. The pivot pin is transversely oriented with respect to the longitudinal axis and coplanar with respect to a plane defined by a tissue contacting surface of the second jaw member.

The band may be fabricated from a material capable of transmitting compressive and tensile loads, such as, for example, spring steel.

The electrosurgical instrument may further include electrodes disposed on the first and the second jaw members. The electrodes may be in juxtaposed relation to one another when the first and the second jaw members are substantially aligned.

The second jaw member may include a pair of spaced apart flanges extending proximally therefrom, wherein each flange may be provided with at least one inter-engaging element. The first jaw member may include a knuckle extending proximally therefrom and may be disposed between the pair of flanges. The band may be pivotably connected to the knuckle at a predetermined location. For example, the predetermined location may be spaced a transverse distance from the pivot pin in the longitudinal axis.

The handle assembly of the electrosurgical instrument may be a reverse pivoting handle.

The electrosurgical instrument may further include a series of linkages configured and adapted to urge the lead screw in a distal direction and drive the actuation shaft in the distal direction when the pivoting handle is squeezed.

The electrosurgical instrument may further include a biasing member operatively associated with the pivoting handle for maintaining and returning the pivoting handle to an un-actuated position.

It is envisioned that at least one of the first and second jaw members includes a longitudinally extending knife blade.

According to another aspect of the present disclosure, a bipolar electrosurgical instrument including an end effector is provided. The instrument includes a first pivotable jaw member; and a second pivotable jaw member operatively associated with the first jaw member. The first and second jaw members are movable between a first orientation in which the first and second jaw members are axially aligned with a longitudinal axis of the instrument, and at least one second orientation in which the first and second jaw members are angled with respect to the longitudinal axis of the instrument. Each jaw member includes an electrode operatively associated therewith and defines tissue contacting surfaces in juxtaposed relation to one another. The first and second jaw members have an open condition in which the first and second jaw members are relatively spaced from one another and a closed condition in which the first and second jaw members are relatively close to one another The instrument further includes a locking mechanism operatively associated with the second jaw member. The locking mechanism has a first position in which the locking mechanism engages the second jaw member and prevents movement of the second jaw member, and a second position in which the locking mechanism is disengaged from the second jaw member and allows for movement of the second jaw member between the first orientation and the at least one second orientation.

The instrument further includes an actuation mechanism operable to move the first jaw member between the first orientation and the at least one second orientation.

The locking mechanism includes a locking shaft having a distal end operatively associated with the second jaw member; and a locking pin extending transversely from the distal end of the locking shaft. The locking pin is selectively engagable between a plurality of inter-engagement elements provided on the second jaw member. Accordingly, when the locking mechanism is in the first position, the locking pin is engaged with one of the plurality inter-engagement elements of the second jaw member. Additionally, when the locking mechanism is in the second position, the locking pin is disengaged from the inter-engaging elements of the second jaw member.

The actuation mechanism may include an actuation shaft rotatably disposed within the locking shaft, wherein the actuation shaft includes a distal end and a proximal end; and a band having a proximal end operatively connected to the distal end of the actuation shaft, and a distal end extending through an aperture formed in the distal end of the locking shaft and operatively connected to the first jaw member. Accordingly, when the actuation shaft is displaced in one of an axially proximal and distal direction, the first jaw member is articulated between the first orientation and the at least one second orientation.

The electrosurgical instrument may further include an articulation knob operatively supported at a proximal end of the instrument. The articulation knob may be operatively associated with the locking mechanism and the actuation mechanism. Accordingly, the articulation knob effectuates independent operation of at least one of the locking mechanism and the actuation mechanism. It is envisioned that axial displacement of the articulation knob results in movement of the locking mechanism between the first and second positions. It is further envisioned that rotation of the articulation knob may move the actuation mechanism to move the first jaw member between the first orientation and the at least one second orientation.

The locking mechanism may include a first collar operatively connected to a proximal end of the locking shaft; a pair of diametrically opposed connecting rods extending proximally from the first collar; and a second collar operatively connected to at least one connecting rod. The second collar is rotatably supported on the articulation knob, wherein as the articulation knob is axially displaced in one of the proximal and distal directions, the connecting rods transmit the axial displacement of the articulation knob to the locking rod.

The actuation mechanism may further include a lead screw operatively connected to a proximal end of the actuation shaft; and a drive shaft operatively interconnecting the lead screw and the articulation knob. Accordingly, as the articulation knob is rotated, the drive shaft transmits rotation to the lead screw and the lead screw converts rotation thereof into the axial displacement of the actuation shaft.

The electrosurgical instrument may further include an indexing plate operatively supported between the pair of connecting rods and operatively engagable with the articulation knob. The indexing plate defines a plurality of angular orientations for the second jaw member.

The second jaw member may be biased to the axially aligned orientation.

The end effector may include a pivot pin extending through the first and second jaw members. The pivot pin may be transversely oriented with respect to the longitudinal axis of the instrument and coplanar with respect to a plane defined by the tissue contacting surface of the second jaw member.

According to a further aspect of the present disclosure, a bipolar electrosurgical instrument is provided. The instrument includes an end effector operatively associated with a distal end of a shaft. The end effector includes a first jaw member pivotably coupled to a distal end of the shaft; a second jaw member pivotably coupled to the distal end of the shaft, wherein at least one of the first and the second jaw members comprise a plurality of inter-engagement elements; and a plurality of electrodes with at least one electrode being operatively disposed on the first jaw member and at least another electrode being operatively disposed on the second jaw member, wherein the electrodes transmit radio frequency energy therebetween. The first and second jaw members move from a first orientation in which the first and the second jaw member are axially aligned with a longitudinal axis of the shaft and a plurality of second orientations in which the first and the second jaw members are angled with respect to the longitudinal axis. The first and second jaw members have an open condition in which the first and second jaws members are spaced from one another and a closed condition in which the first and second jaw members are substantially in close proximity to one another.

The instrument further includes a locking mechanism operatively associated with the second jaw member to prevent movement of the second jaw member between the first orientation and any of the plurality of second orientations, and a second position in which the locking mechanism is disengaged from the second jaw member and allows for movement of the second jaw member between the first orientation and any of the plurality of second orientations.

The instrument still further includes an actuation mechanism operatively connected to at least one of the first jaw member and second jaw member. The actuation mechanism is operable to move at least one of the first jaw member and second jaw member between the first orientation and the plurality of second orientations.

According to yet another aspect of the present disclosure, a bipolar electrosurgical instrument is provided. The instrument includes an end effector operatively associated with a distal end of a shaft. The end effector includes a first jaw member pivotably coupled to a distal end of the shaft; a second jaw member pivotably coupled to the distal end of the shaft; and a plurality of electrodes with at least one electrode being operatively disposed on the first jaw member and at least another electrode being operatively disposed on the second jaw member, wherein the electrodes transmit radiofrequency energy therebetween. The end effector defines a longitudinal axis with the shaft when the end effector is in a coaxial position. The end effector is articulatable from an angle of about 0° with respect to the longitudinal axis to an angle of about 60° with respect to the longitudinal axis. Additionally, the first and the second jaw members are adapted to move between an open position and a closed position at any of a plurality of angular positions of the end effector.

The first and second jaw members may be openable and closable. The end effector may articulate by a single linkage.

The electrosurgical instrument may further include a locking device for locking the end effector at any of the plurality of angular positions.

The electrosurgical instrument may still further include a cutting device. The cutting device may traverse through a channel in at least one the first and the second jaw members.

The end effector may have a predetermined size to be introduced and articulate in a pulmonary tissue region. The end effector with the predetermined size may be configured to apply radiofrequency energy in the pulmonary tissue region. The end effector with the predetermined size may form a lung parenchyma seal in the pulmonary tissue region.

Other objects and features of the present disclosure will become apparent from consideration of the following description taken in conjunction with the accompanying drawings.

BRIEF DESCRIPTION OF THE DRAWINGS

By way of example only, embodiments of the electrosurgical instrument of the present disclosure will be described with reference to the accompanying drawings, in which.

DETAILED DESCRIPTION

Figure 1:
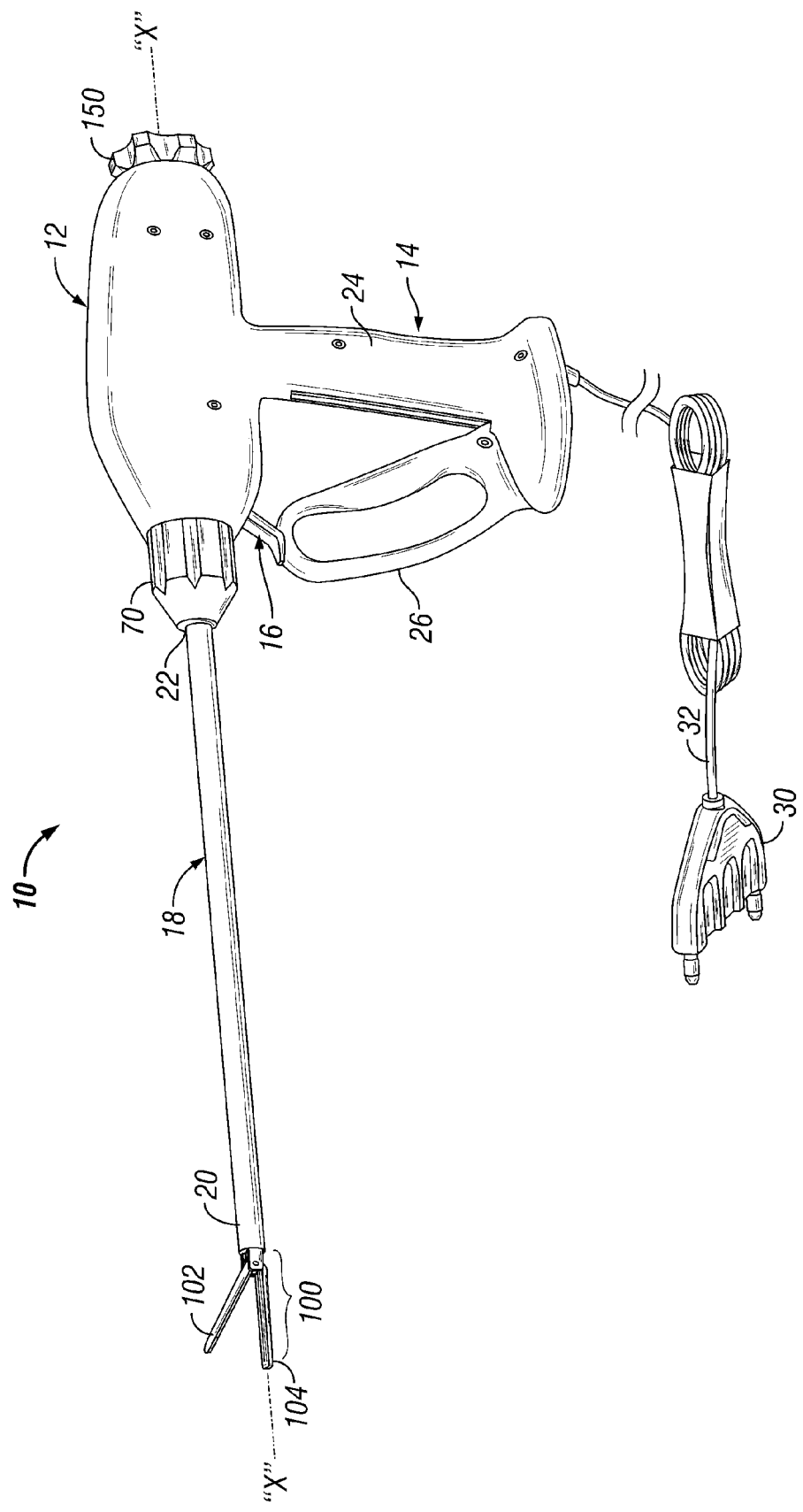
FIG. 1 is a perspective view of an articulating bipolar electro-surgical instrument according to an embodiment of the present disclosure.
Figure 2:
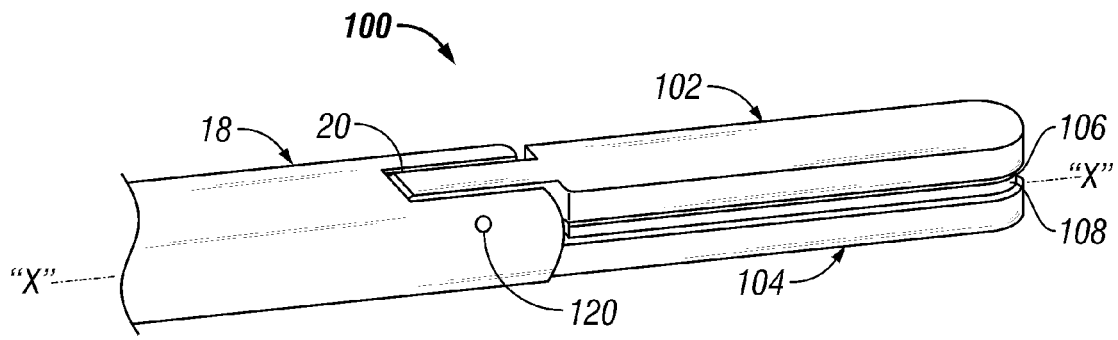
FIG. 2 is an enlarged, right side perspective view of a distal end of the surgical instrument of FIG. 1, including an end effector in accordance with an embodiment of the present disclosure, depicting a pair of opposed jaw members thereof in an axially aligned orientation and in a closed condition.

Detailed embodiments of the presently disclosed instruments, devices and systems will now be described in detail with reference to the drawing figures wherein like reference numerals identify similar or identical elements. In the drawings and in the description which follows, the term "proximal", as is traditional, will refer to the end of the instrument, device and/or system which is closest to the operator while the term "distal" will refer to the end of the instrument, device and/or system which is furthest from the operator.

Referring to FIG. 1, a bipolar electro-surgical instrument, according to an embodiment of the present disclosure, is shown generally as 10. Electro-surgical instrument 10 generally includes a housing 12, a handle assembly 14, an activation assembly 16, and an end effector 100, in accordance with the present disclosure, which operates to grasp, seal and/or cut tissue.

More particularly, instrument 10 includes a shaft 18, defining a longitudinal "X" axis, which has a distal end 20 dimensioned to mechanically engage end effector 100 and a proximal end 22 which mechanically engages housing 12. Instrument 10 also includes an electrical interface or plug 30 which connects instrument 10 to a source of electrosurgical energy, e.g., an electrosurgical generator (not shown). An electrical cable 32 extends from plug 30 and is securely connected to housing 12 of instrument 10. Cable 32 is internally divided within housing 12 to transmit electrosurgical energy through various electrical feed paths (not shown) to end effector 100. Handle assembly 14 includes a fixed handle 24 and a movable handle, e.g., a reverse pivot handle 26. Fixed handle 24 is integrally associated with housing 12 and movable handle 26 is displaceable relative to fixed handle 24 to actuate a pair of opposing jaw members 102 and 104 of end effector 100.

A collar 70 is operatively mounted to the proximal portion of housing 12 in a manner such that rotation of collar 70 will cause corresponding rotation of shaft 18 to increase the range of operability of surgical instrument 10.

Turning now to FIGS. 2-7, an end effector in accordance with an embodiment of the present disclosure is generally designated as 100. As briefly mentioned above, end effector 100 includes a first or upper jaw member 102 and a second or lower jaw member 104 pivotably associated with one another and pivotably associated with distal end 20 of shaft 18. Each jaw member 102, 104 has a respective electrode 106, 108 in juxtaposed relation to one another. Each electrode 106, 108 defines a respective tissue contacting surface 106a, 108a (see FIG. 3).

Figure 6:
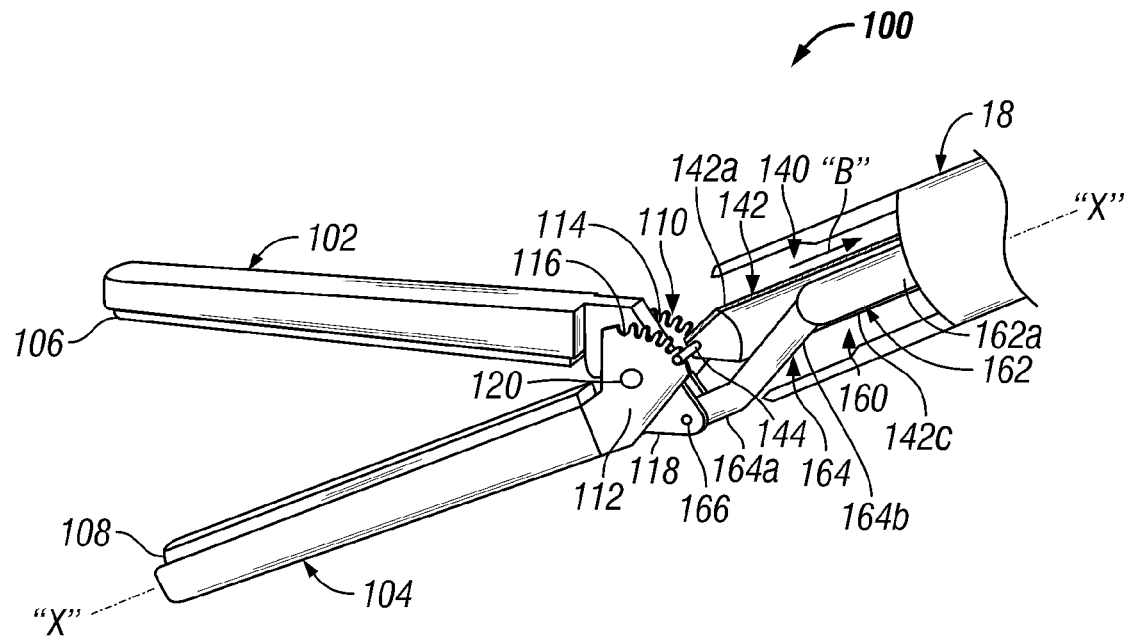
FIG. 6 is a left side perspective view of the end effector of FIGS. 2-5, with a portion of the outer tube broken away and/or removed in order to illustrate the locking mechanism and the articulating mechanism of the present disclosure.
Figure 7:
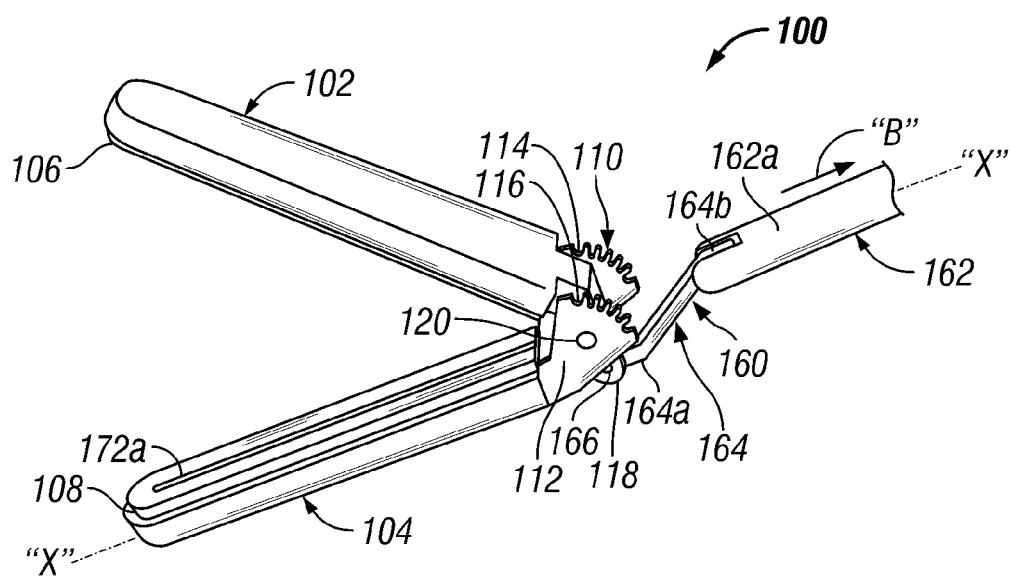
FIG. 7 is a left side perspective view of the end effector of FIGS. 2-6, with the outer tube and locking shaft entirely removed in order to further illustrate the articulating mechanism of FIG. 6.

As best seen in FIGS. 6 and 7, the proximal end of second jaw member 104 includes a yoke 110 defined by a pair of opposed, spaced apart flanges 112, 114 which extend therefrom. Preferably, flanges 112, 114 are at least substantially orthogonally oriented with respect to a plane defined by tissue contacting surface 108a and at least substantially parallel to the longitudinal "X" axis of shaft 18. Each flange 112, 114 defines an arcuate edge including at least one, preferably a plurality of, inter-engaging element(s) 116, such as, for example, gears, teeth, or the like.

First jaw member 102 includes a knuckle 118 extending from a proximal end thereof. Knuckle 118 is configured and dimensioned to be positionable between flanges 112, 114. First jaw member 102 and second jaw member 104 are pivotably connected to one another by a pivot pin 120 extending through flanges 112, 114 and knuckle 118. Pivot pin 120 defines a pivot axis "Z" (see FIG. 3) which is oriented in a direction at least substantially orthogonal to the longitudinal "X" axis of shaft 18 and is in a plane which is at least substantially parallel to the plane defined by tissue contacting surface 108a. Preferably, pivot pin 120 extends through the longitudinal "X" axis of shaft 18.

Figure 5:
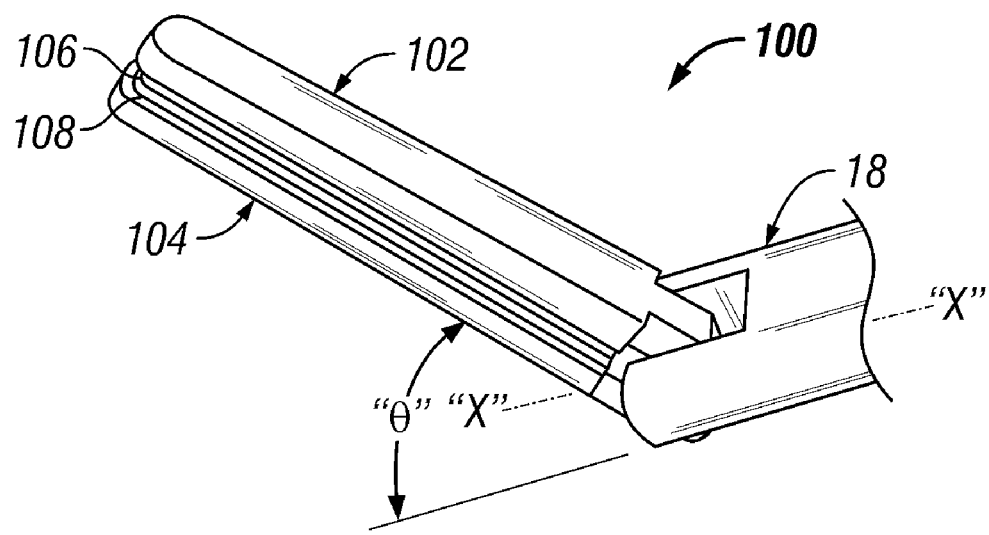
FIG. 5 is a left side perspective view of the end effector of FIGS. 2-4, depicting the pair of opposed jaw members in an articulated orientation and in a closed condition.

Preferably, second jaw member 104 is biased to an angled orientation with respect to the longitudinal "X" axis, as seen in FIG. 5, by a biasing member (not shown), such as, for example, a spring. The biasing member tends to maintain second jaw member 104 angled with respect to the central longitudinal "X" axis.

Figure 8:
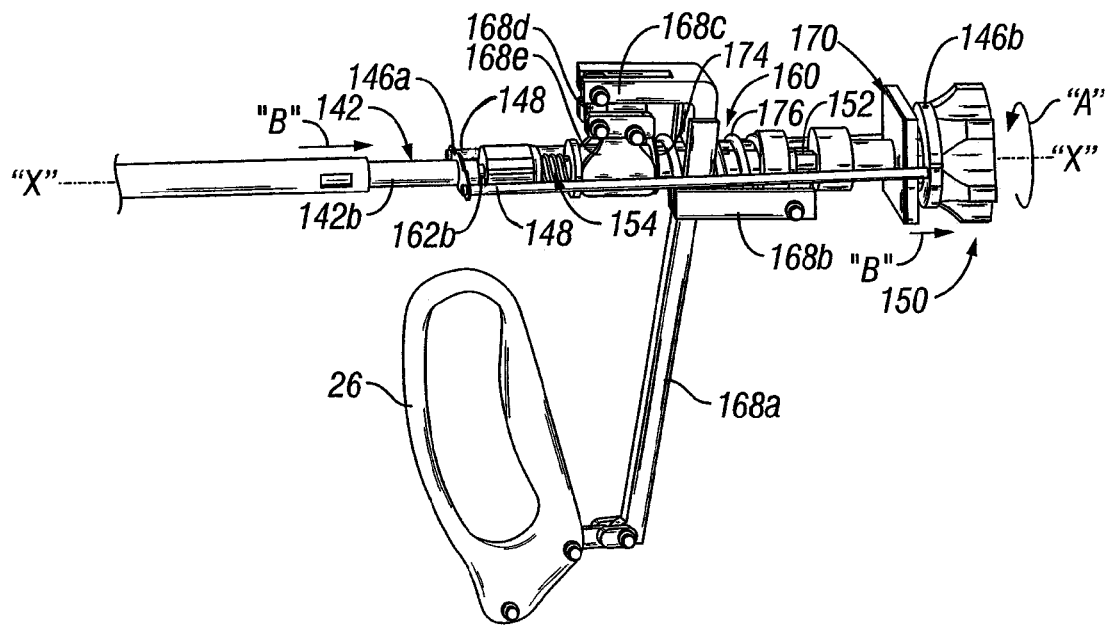
FIG. 8 is a perspective view of the locking mechanism and articulating mechanism according to an embodiment of the present disclosure.

Preferably, instrument 10 is provided with a locking mechanism 140 for maintaining second jaw member 104 in an axially aligned orientation or in any number of angled orientations with respect to the longitudinal "X" axis. Preferably, the angled orientations include orientations up to a 90° orientation with respect to the longitudinal "X" axis and, more preferably, orientations up to a 60° orientation with respect to the longitudinal "X" axis. As seen in FIGS. 6 and 8, locking mechanism 140 includes an articulation locking shaft 142 having a distal end 142a, and a locking pin 144 extending from distal end 142a of locking shaft 142, preferably, diametrically from either side of distal end 142a of locking shaft 142. Preferably, locking shaft 142 is sized and positioned to be disposed between flanges 112, 114 of second jaw member 104 and locking pin 144 extends from either side of distal end 142a of locking shaft 142 an amount sufficient to selectively engage inter-engaging element(s) 116 of flanges 112, 114.

Locking mechanism 140 has a first position in which locking shaft 142 is in a distally advanced position such that locking pin 144 engages inter-engaging element(s) 116 of flanges 112, 114 and thereby prevents articulation (e.g., pivoting, angular displacement or rotational displacement) of second jaw member 104 with respect to the central longitudinal "X" axis, and at least one second position in which locking shaft 142 is proximally spaced from the first distally advanced position such that locking pin 144 is disengaged from inter-engaging element(s) 116 of flanges 112, 114 and thereby permits articulation (e.g., pivoting, angular displacement or rotational displacement) of second jaw member 104, about pivot pin 120, with respect to the central longitudinal "X" axis to any number of angled or articulated orientations.

As seen in FIG. 8, a proximal end 142b of locking shaft 142 is rotatably coupled to and/or otherwise journaled in a first or distal collar 146a. A pair of connecting rods 148 interconnect first collar 146a with a second or proximal collar 146b (see FIGS. 8 and 9). Preferably, connecting rods 148 extend along either side of an actuation mechanism and/or linkage 160. Second collar 146b is rotatably coupled to and/or otherwise journaled in an annular channel formed in an articulation knob 150.

The articulation knob 150 is operatively supported on a proximal end of housing 12. Articulation knob 150 defines a central axis of rotation which is preferably axially aligned with the longitudinal "X" axis.

Turning now to FIGS. 6-9, instrument 10 is further provided with an actuation mechanism 160 to effectuate articulation (e.g., angular movement and/or rotation) of first jaw member 102 about pivot pin 120. Actuation mechanism 160 includes an actuation shaft 162 reciprocatingly received in locking shaft 142 of locking mechanism 140 (FIG. 6). Actuation shaft 162 includes a distal end 162a operatively connected to knuckle 118 of first jaw member 102, and a proximal end 162b operatively connected to a lead screw 154 of actuation mechanism 160 (FIG. 8). Actuation mechanism further includes a drive shaft 152 inter-connecting articulation knob 150 and lead screw 154.

In particular, actuation mechanism 160 includes a linkage 164 having a distal end 164a, extending through an aperture 142c formed in distal end 142a of locking shaft 142 and pivotably connected to knuckle 118 of first jaw member 102 by a pivot pin 166, and a proximal end 164b, pivotably connected to distal end 162a of actuation shaft 162. Preferably, pivot pin 166 is spaced a transverse distance from pivot pin 120. Linkage 164 has an angled shape for increased leverage.

In operation, as seen in FIGS. 6-9 and as will be described in greater detail below, articulation knob 150 performs two functions: the first function being the articulation of first jaw member 102 and second jaw member 104, between an axially aligned orientation and a plurality of angled orientations; and the second function being the locking of second jaw member 104 in the axially aligned orientation or any of the plurality of angled orientations.

The first function of articulation knob 150 is performed as a result of rotation of articulation knob 150. As articulation knob 150 is rotated in the direction of arrow "A" (see FIG. 8), articulation knob 150 rotates drive shaft 152 which, in turn, rotates lead screw 154. As lead screw 154 is rotated in the direction of arrow "A", lead screw 154 is displaced in a proximal direction, extending the distance between pivot 166 and cam 168. Lead screw 154 also desirably lengthens shaft 162 so that the force applied to the compression spring 176 during activation remains consistent. As discussed below, predetermined pressure applied to the tissue optimizes tissue sealing. As actuation shaft 162 is displaced in an axially proximal direction, first jaw member 102 is articulated and/or pivoted about pivot pin 120 between an orientation in which first jaw member 102 is at least substantially axially aligned with the longitudinal "X" axis (see FIG. 2), and a plurality of orientations in which first jaw member 102 is angled with respect to the longitudinal "X" axis (see FIGS. 3-7).

With pin 144 engaged in engaging elements 116, the pivoting of first jaw member 102 occurs separately from second jaw member 104, which remains stationary. With pin 144 disengaged from engaging elements 116, the pivoting of first jaw member 102 and second jaw member 104 occurs jointly, as the second jaw member 104 is connected to the first jaw member 102 through the biasing member. The degree to which first jaw member 102 and second jaw member 104 is angled is dependent upon the amount that articulation knob 150 is rotated.

The second function of articulation knob 150 is performed as a result of axial displacement of articulation knob 150 in the direction of, and opposite to the direction of, arrow "B". As articulation knob 150 is displaced in the direction of arrow "B" (i.e., in a proximal direction), articulation knob 150 pulls on connecting rods 148 which, in turn, pull on locking shaft 142. As locking shaft 142 is displaced in the direction of arrow "B", locking pin 144 is disassociated and/or otherwise disengaged from inter-engagement element(s) 116. In so doing, the biasing member (not shown) is free to urge second jaw member 104 about pivot pin 120, from an axially aligned orientation (see FIGS. 2-4, 6 and 7) to an angled and/or articulated orientation (see FIG. 5) as first jaw member 102 is articulated by rotation of articulation knob 150.

Once second jaw member 104 has been angled and/or articulated, articulation knob 150 is displaced in a direction opposite to arrow "B" (e.g., driven forward) in order to drive locking shaft 142 in a distal direction and re-engage locking pin 144 with inter-engagement element(s) 116 of flanges 112, 114. In so doing, second jaw member 104 is fixed in the needed and/or desired angle "Θ" (see FIG. 5), and jaw member 102 may be pivoted separately.

Actuation shaft 162 is also axially displaced as a result of the manipulation of reverse pivot handle 26 (FIG. 8) and subsequent manipulation of actuation mechanism 160. In particular, as pivot handle 26 is squeezed, linkages 168a-168e (see FIG. 8) of actuation mechanism 160 are manipulated in such a manner so as to drive actuation shaft 162 in the proximal direction to pivot first jaw member 102 about pivot pin 120.

Desirably, a cam plate 174 is provided which is urged in a proximal direction, against the force of a biasing member 176 (e.g., a tensile loading spring), as pivot handle 26 is squeezed. In this manner, when pivot handle 26 is released, cam plate 174 is urged in a distal direction by biasing member 176 thereby urging actuation shaft 162 distally and, in turn, opening end effector 100 (e.g., spacing first jaw member 102 from second jaw member 104). Additionally, biasing member 176 tends to return and/or maintain pivot handle 26 in an unsqueezed and/or un-actuated condition.

Figure 9:
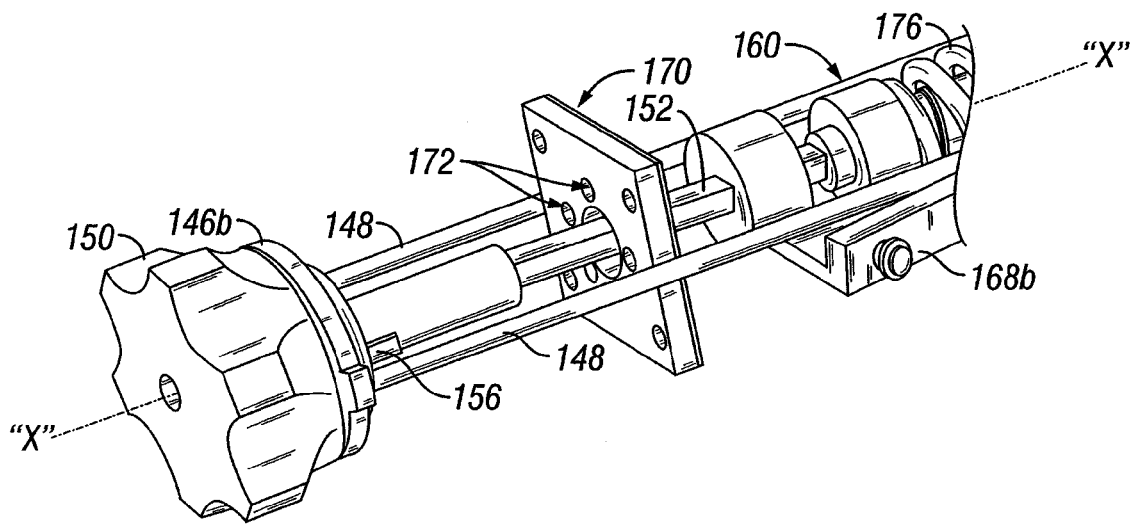
FIG. 9 is a rear perspective view of the locking mechanism and articulating mechanism of FIG. 8.
Figure 10:
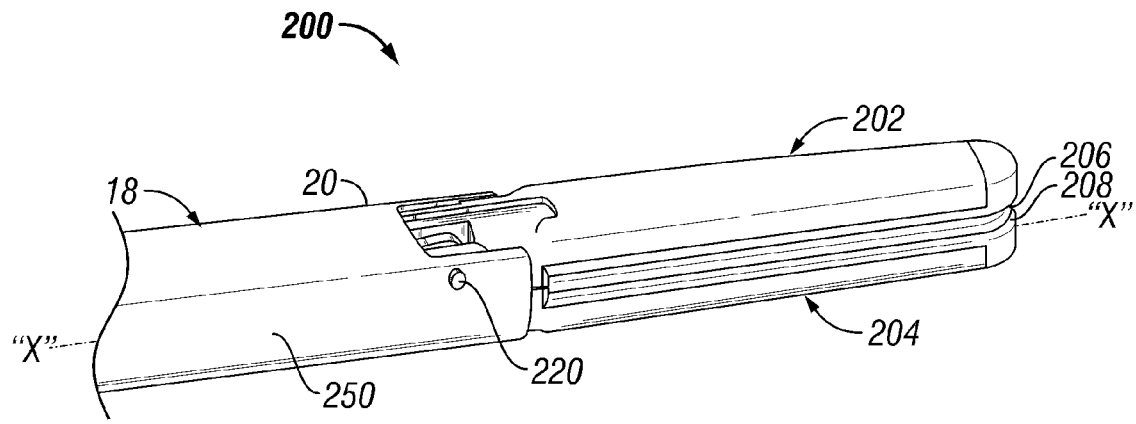
FIG. 10 is an enlarged, right side perspective view of a distal end of a surgical instrument including an end effector, in accordance with an alternate embodiment of the present disclosure, showing a pair of opposed jaw members, in an axially aligned orientation.

As seen in FIGS. 8 and 9, instrument 10 may be provided with an indexing plate 170 operatively associated with articulation knob 150. Indexing plate 170 includes a plurality of openings 172 formed at particular and/or discrete locations therein. Openings 172 are configured and dimensioned to selectively receive a pin 156 (see FIG. 9) extending distally from articulation knob 150. In use, as articulation knob 150 is rotated, pin 156, extending from articulation knob 150, selectively engages openings 172 of indexing plate 170 in order to define predetermined angular orientations for first jaw member 102. Preferably, openings 172 of indexing plate 170 are "clocked" (i.e., correspond with) the position of inter-engagement element(s) 116 of flanges 112, 114. In use, pin 156 is disengaged from openings 172 by pulling articulation knob 150 in a proximal direction.

Indexing plate 170 preferably includes a pair of recesses 178 (see FIG. 9) formed therein for receipt and slidable engagement with rods 148. Recesses 178 and rods 148 inter-engage with one another to thereby prevent rotation of indexing plate 170 about the longitudinal "X" axis and maintain the relative position of openings 172 with respect to articulation knob 150. In this manner, the discrete angular positions of second jaw member 104, for each position of opening 172, is maintained.

With reference to FIGS. 1-9, use and operation of instrument 10 will now be described in greater detail. Initially, with first and second jaw members 102, 104 of end effector 100 in a substantially axially aligned condition, end effector 100 of surgical instrument 10 is introduced into an operative site, e.g., the thoracic cavity, through a port or the like (not shown).

Once introduced into the operative site, and in the open jaw configuration, as briefly described above, articulation knob 150 is rotated in the direction of arrow "A" (see FIG. 8) to pivot and/or articulate first jaw member 102 about pivot pin 120. As articulation knob 150 is rotated in the direction of arrow "A", drive shaft 152 rotates lead screw 154 and, in turn, moves actuation shaft 162, in the direction opposite of arrow "B" (i.e., in a distal direction). As actuation shaft 162 is displaced in a distal direction, first jaw member 102 and second jaw member 104 are pivoted about pivot pin 120 to a desired and/or needed angled and/or articulated orientation. Aligning articulation knob 150 with indexing positions on indexing plate 170 will allow connecting rods 148 and locking shaft 142 to move distally and place pin 144 in recess 116.

With end effector 100 in the open condition, instrument 10 may be manipulated to place end effector 100 about the tissue to be treated, i.e., to place first and second jaw member 102, 104 on either side of the tissue to be treated. With end effector so positioned, articulation knob 150 is displaced in the direction of arrow "B", i.e., withdrawn in a proximal direction, to permit rotation and/or articulation of second jaw member 104, under the influence of the biasing member (not shown), about pivot pin 120. In particular, as articulation knob 150 is drawn in the proximal direction, connecting rods 148 and, in turn, locking shaft 142 are displaced in a proximal direction until locking pin 144 is disassociated and/or otherwise disengaged from inter-engagement element(s) 116 of second jaw member 104.

Preferably, instrument 10 is configured and dimensioned to permit pivoting of first jaw member 102 and, in turn, second jaw member 104, to an angle "Θ" (see FIG. 5) of from at least about 0° to at least about 60°, relative to the longitudinal "X" axis. For example, pulling on knob 150 releases second jaw member 104, which is free to rotate away from an axially-aligned position. Most preferably, indexing plate 170 is configured to inter-engage with articulation knob 150 such that first jaw member 102 and, in turn, second jaw member 104, are articulated in predetermined increments; for example, 10° increments may be used.

If needed and/or desired, end effector 100 may be rotated about the longitudinal "X" axis by rotating collar 70 (see FIG. 1) about the longitudinal "X" axis. In so doing, the user does not have to rotate the entirety of instrument 10, including housing 12, about the longitudinal "X" axis.

Closing and clamping of end effector 100 is accomplished by squeezing handle 26. In particular, as seen in FIGS. 7 and 8, as handle 26 is squeezed linkages 168a-168e of actuation mechanism 160 are manipulated in such a manner so as to move actuation shaft 162 in a proximal direction. Movement of actuation shaft 162 in a proximal direction results in pivoting of first jaw member 102 about pivot pin 120, thereby at least substantially approximating tissue contacting surface 106a of first jaw member 102 toward tissue contacting surface 108a of second jaw member 104.

With end effector 100 clamped onto the tissue to be treated, RF energy may then be transmitted to electrodes 106, 108 of first and second jaw members 102, 104, respectively, to seal or fuse the tissue to be treated. By way of example only, the RF energy may be activated by squeezing activation assembly 16 (see FIG. 1). Following sealing of the tissue to be treated, the handle member is moved forward to re-open end effector 100 and/or otherwise space first jaw member 102 from second jaw member 104 and thereby release the treated tissue therefrom. The process may be repeated as many times as necessary depending on the particular surgical procedure and/or depending on a particular surgical purpose.

Alternatively, following the surgical procedure and/or when desired, first and second jaw members 102, 104 are returned to the axially aligned orientation in order to withdraw surgical instrument 10 and, in turn, end effector 100, from the operative site. Instrument 10 is manipulated to space end effector 100 from the treated tissue, i.e., to position end effector 100 such that first and second jaw members 102, 104 are free to rotate and are not obstructed by other tissue and/or body organs.

With end effector 100 so positioned, articulation knob 150 is displaced in the proximal direction, i.e., in the direction of arrow "B", to once again free second jaw member 104 to rotate about pivot pin 120. Then, articulation knob 150 is rotated in a direction opposite to arrow "A" in order to pivot first jaw member 102 from the angled and/or articulated orientation to the axially aligned orientation. In so doing, first jaw member 102 engages second jaw member 104 and causes second jaw member 104 to be pivoted from the angled orientation to the axially aligned orientation. Once first and second jaw members 102, 104 are returned to the axially aligned orientation, instrument 10 and, in turn, end effector 100, may be withdrawn from the operative site.

Figure 3:
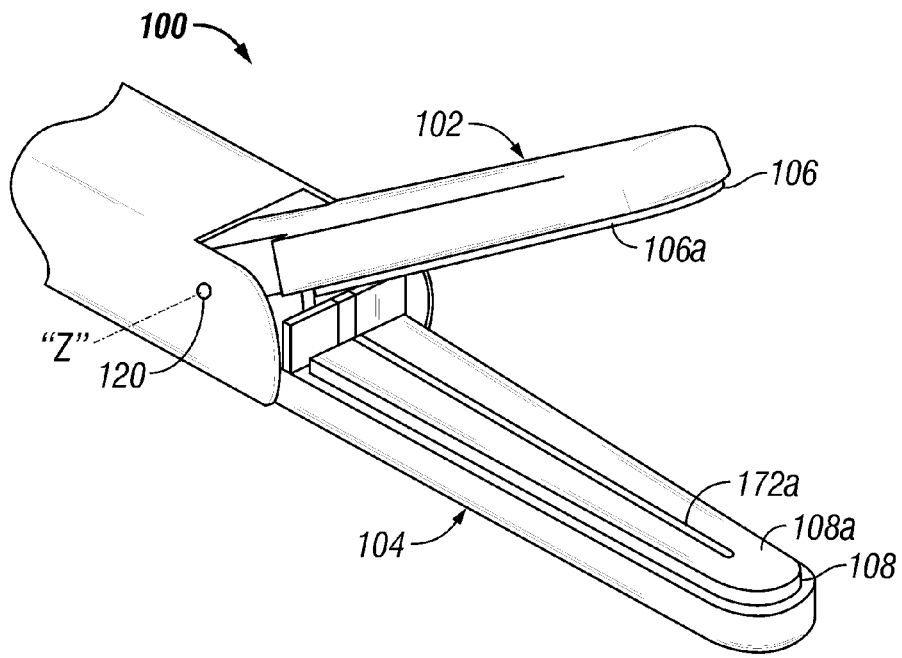
FIG. 3 is an enlarged, front perspective view of the end effector of FIG. 2, depicting a first of the pair of opposed jaw members in the axially aligned orientation and a second of the pair of opposed jaw members in an angled or open condition.
Figure 4:
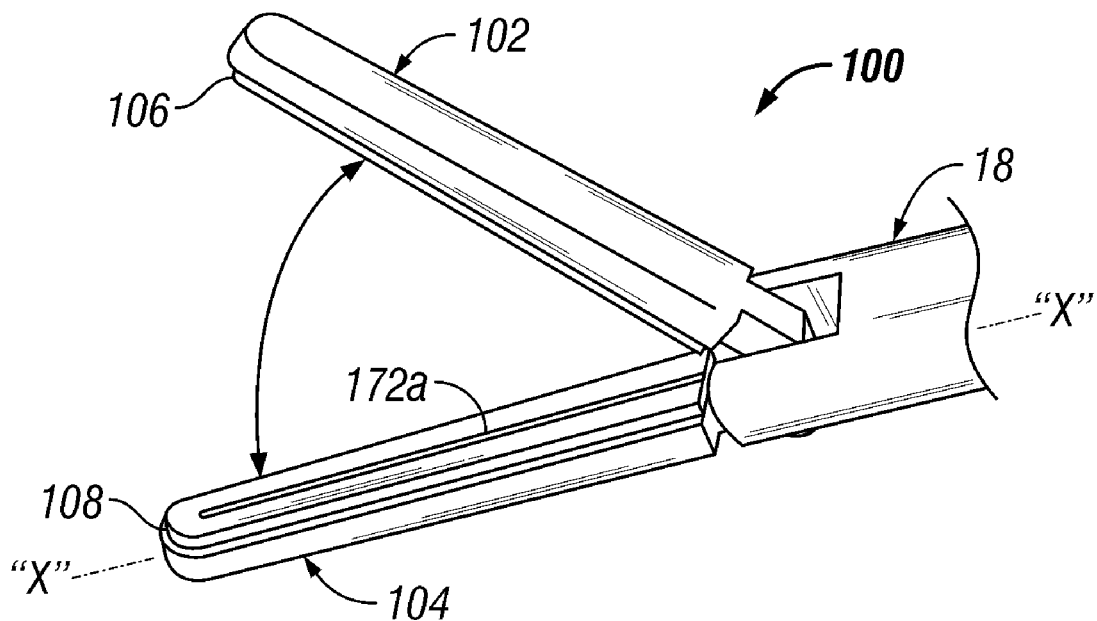
FIG. 4 is a left side perspective view of the end effector of FIGS. 2-3, depicting the a first of the pair of opposed jaw members in the axially aligned orientation and a second of the pair of opposed jaw members in an angled or open condition.

It is envisioned that one of the first and second jaw members 102, 104, preferably second jaw member 104, is provided with a reciprocating knife assembly (not shown), operatively associated therewith. As best seen in FIGS. 3, 4 and 7, second jaw member 104 defines a longitudinally oriented knife track 172a formed in tissue contacting surface 108a of electrode 108, which preferably extends proximally beyond tissue contacting surface 108a of second jaw member 104.

The knife assembly may include a carrier slidably disposed within second jaw member 104. The carrier is preferably fabricated from a flexible, pliable and/or resilient material such that the carrier may flex and/or bend with the articulation of first and second jaw members 102, 104. The knife assembly preferably further includes a knife blade extending from the carrier and through knife track 172a. For example, carrier 274 and knife blade 280 discussed below in connection with FIG. 18 may be used in the instrument discussed above.

Preferably, first jaw member 102 is also provided with a longitudinally oriented knife track (not shown) formed in tissue contacting surface 106a of electrode 106. The knife track of first jaw member 102 is desirably disposed in vertical registration with knife track 172a of second jaw member 104 when first jaw member 102 and second jaw member 104 are in close approximation with one another. In this manner, the knife blade is also at least partially received and/or disposed in the knife track of first jaw member 102 when first and second jaw members 102, 104 are approximated toward one another. In addition, as the carrier of the knife assembly is displaced along second jaw member 104, the knife blade is also displaced through knife track 172a and through the knife track of the first jaw member.

Preferably, in operation, following the clamping of the tissue to be treated between first and second jaw members 102, 104 and, preferably following the application of RF energy to the tissue to be treated, the knife assembly is actuated in a manner to drive the carrier and, in turn, the knife blade, in a distal direction, along the entire length of knife track 172a or at least until the knife blade traverses the width of the effected tissue. In so doing, the treated tissue is severed and/or otherwise cut in half. Following cutting of the treated tissue, the knife assembly is actuated to draw the carrier and, in turn, the knife blade, in a proximal direction, preferably to a proximal-most position. It is envisioned that a biasing member (not shown) may be employed to automatically bias the knife in a proximal-most position.

Figure 30:
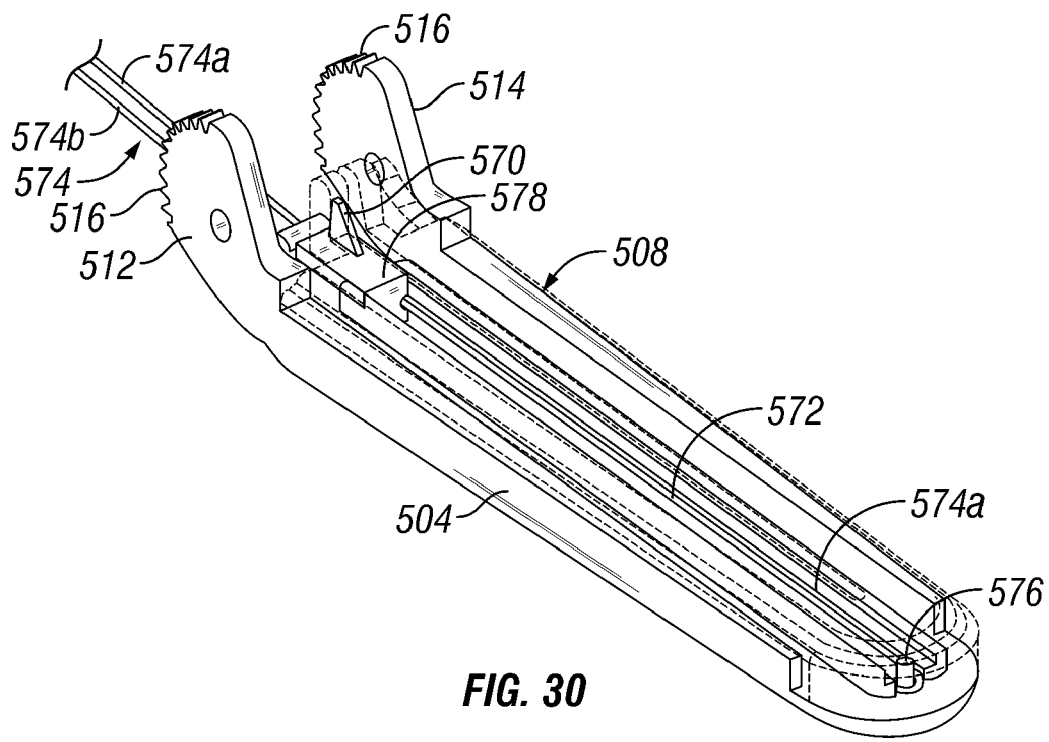
FIG. 30 is an enlarged, transverse, schematic cross-sectional view of an end effector according to another embodiment of the present disclosure, as taken through a pivot axis thereof.
Figure 31:
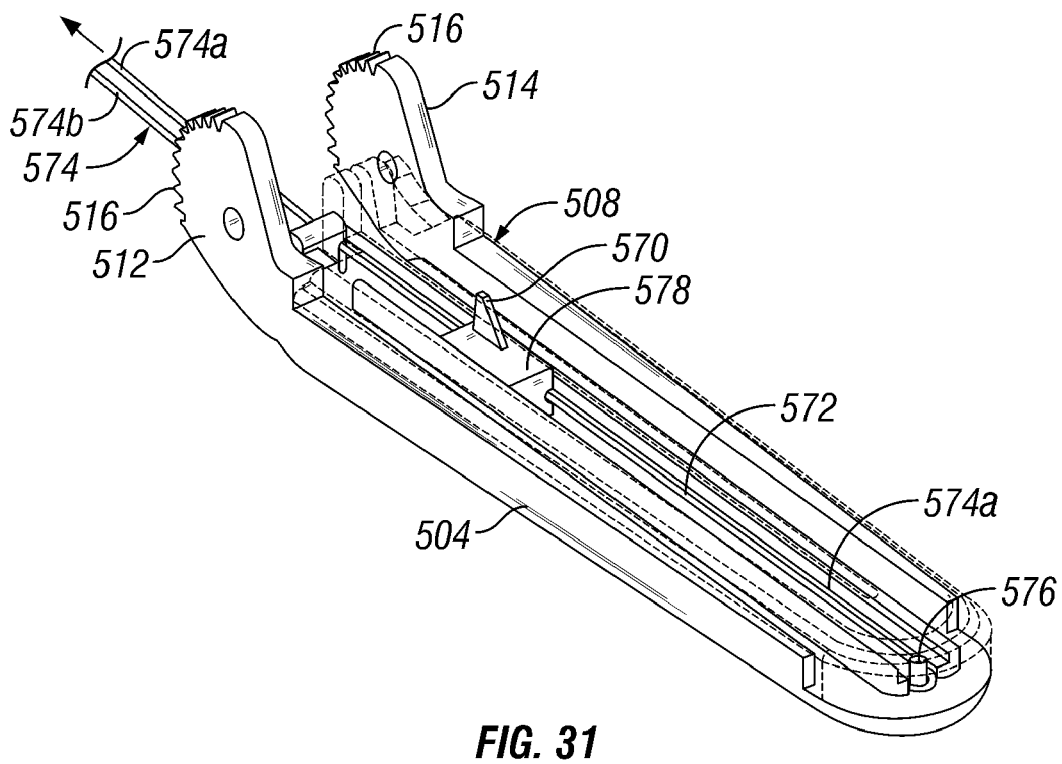
FIG. 31 is an enlarged, transverse schematic cross-sectional view of an end effector according to yet another embodiment of the present disclosure, as taken through a pivot axis thereof.

In further embodiments, carrier member 578 and cable loop 574, as discussed below in connection with FIGS. 30 and 31, are used in the instrument discussed above.

Desirably, use of the knife assembly to sever, divide, cut and/or otherwise separate the tissue, following the application of RF energy, is left to the discretion of the surgeon.

Turning now to FIGS. 10-18, an end effector in accordance with an alternate embodiment of the present disclosure is generally designated as 200. End effector 200 is similar to end effector 100 and will only be discussed in detail to the extent necessary to identify differences in construction and operation. End effector 200 includes a first or upper jaw member 202 and a second or lower jaw member 204 pivotably associated with one another and pivotably associated with distal end 20 of shaft 18. Each jaw member 202, 204 has a respective electrode 206, 208 in juxtaposed relation to one another. Each electrode 206, 208 defines a respective tissue contacting surface 206a, 208a (see FIGS. 12, 14 and 15).

Figure 11:
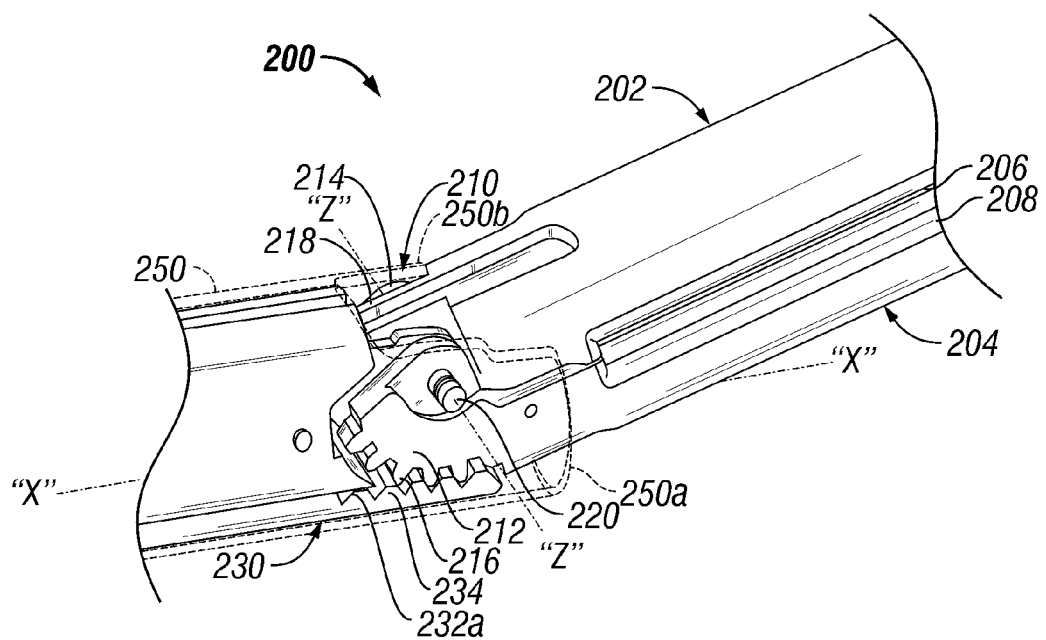
FIG. 11 is an enlarged, right side, perspective view of the end effector of FIG. 10, in an first articulated condition, showing an outer tube shown in phantom to illustrate the internal articulation joint.
Figure 12:
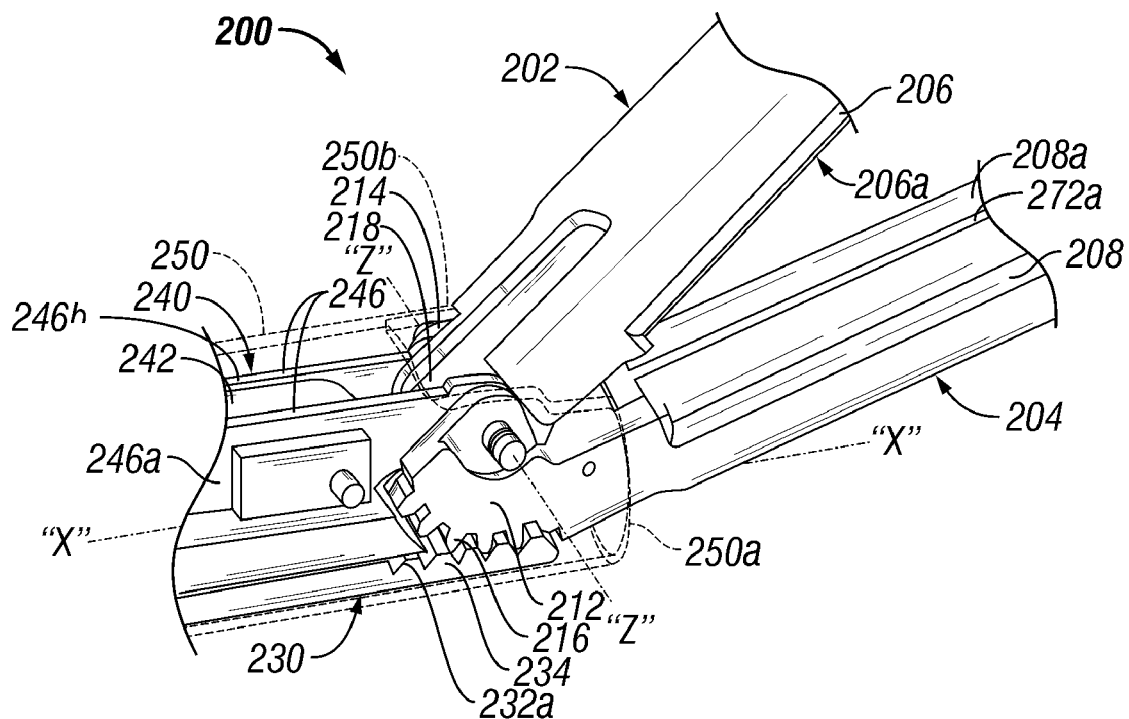
FIG. 12 is an enlarged, right side perspective view of the end effector of FIGS. 10 and 11, illustrating the jaw members in an open condition.
Figure 13:
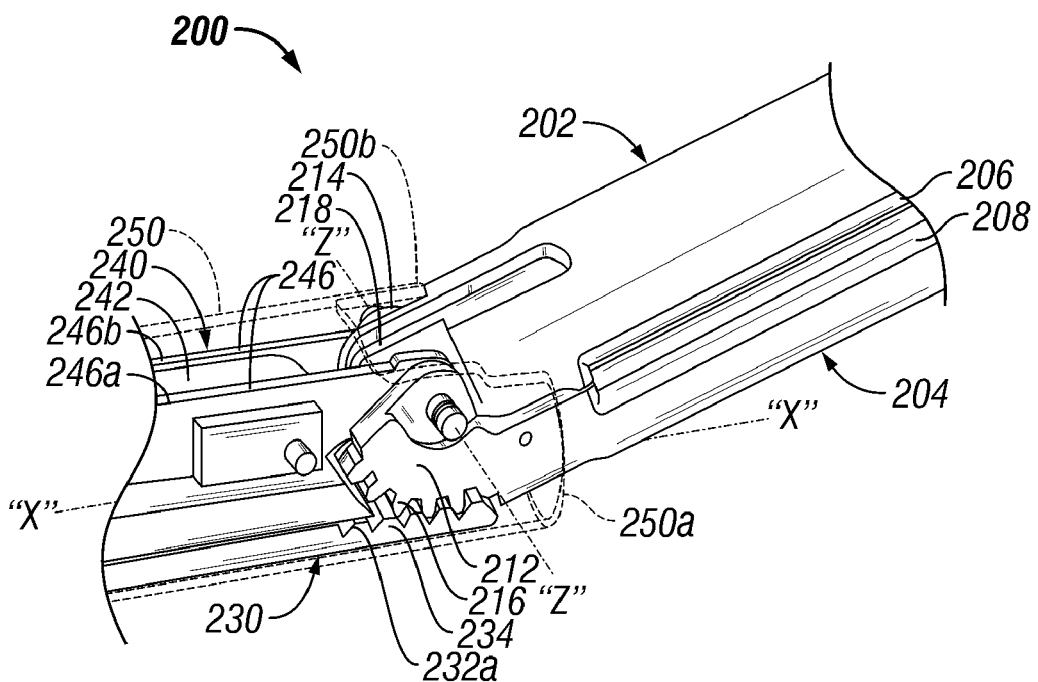
FIG. 13 is an enlarged, right side perspective view of the end effector of FIGS. 10-12, illustrating the jaw members in a closed condition.
Figure 14:
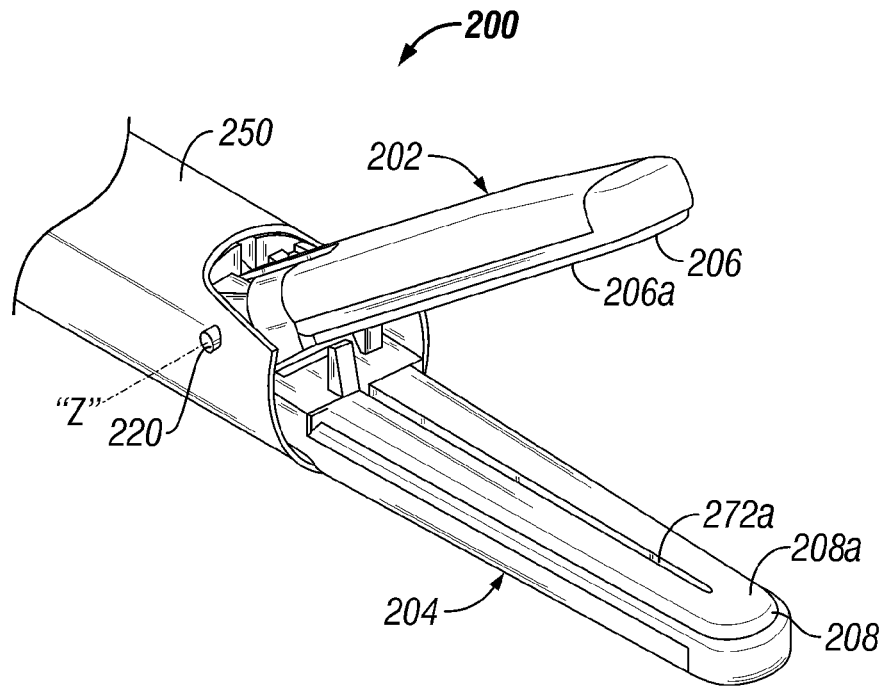
FIG. 14 is an enlarged, front perspective view of the end effector of FIGS. 10-13 showing the jaw members in the axially aligned orientation and with the jaws in the open condition.
Figure 15:
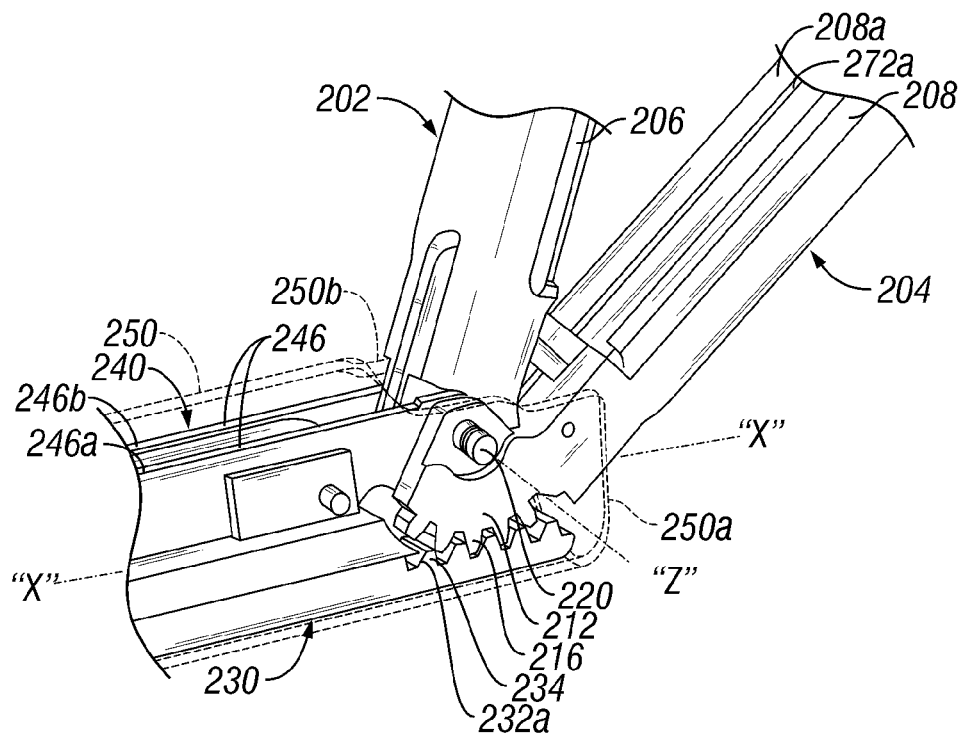
FIG. 15 is an enlarged, right side perspective view of the end effector of FIGS. 10-14, in a second articulated orientation, with the outer tube shown in phantom.
Figure 16:
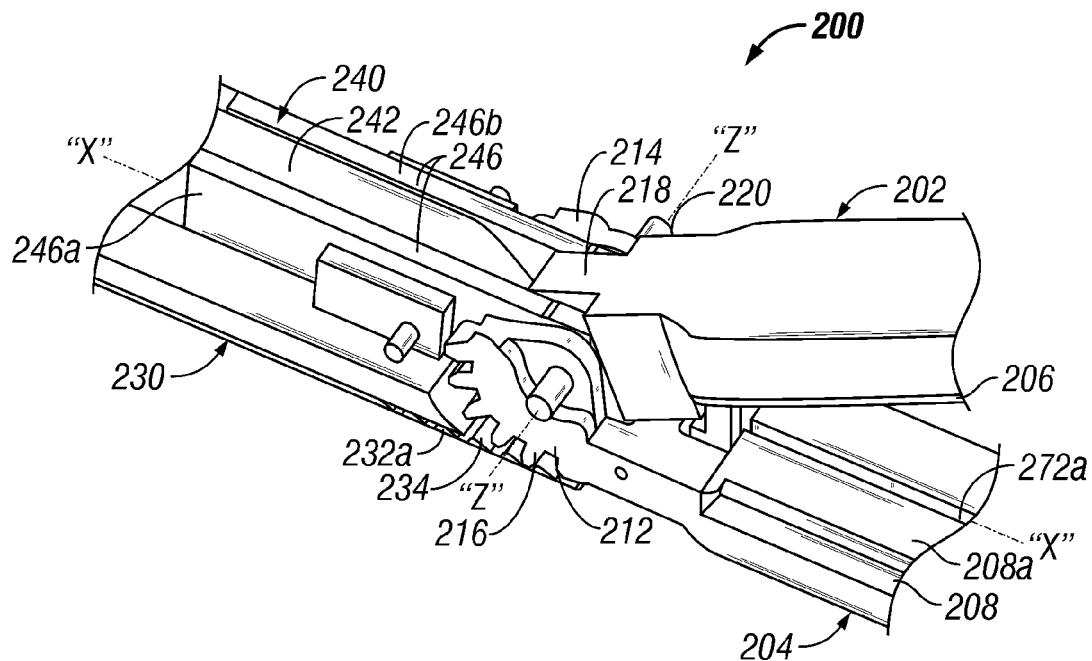
FIG. 16 is an enlarged, top perspective view of the end effector of FIGS. 10-15.

As seen in FIGS. 11-13, the proximal end of second jaw member 204 includes a yoke 210 defined by a pair of opposed, spaced apart flanges 212, 214 which extend therefrom. Preferably, flanges 212, 214 are at least substantially orthogonally oriented with respect to a plane defined by tissue contacting surface 208a and at least substantially parallel to longitudinal axis "X" of shaft 18. Each flange 212, 214 defines an arcuate edge including at least one, preferably a plurality of, engaging element(s) 216, such as, for example, gears or teeth and the like.

First jaw member 202 includes a knuckle 218 extending from a proximal end thereof. Knuckle 218 is configured and dimensioned to be positionable between flanges 212, 214. First jaw member 202 and second jaw member 204 are pivotably connected to one another by a pivot pin 220 extending through flanges 212, 214 and knuckle 218. Pivot pin 220 defines a pivot axis "Z" which is oriented in a direction at least substantially orthogonal to longitudinal axis "X" of shaft 18 and is in a plane which is at least substantially parallel to the plane defined by tissue contacting surface 208a. Preferably, pivot pin 220 extends across longitudinal axis "X" of shaft 18.

As best seen in FIGS. 11-13 and 15-18, an articulation rack 230 is provided which extends through and is slidably associated with shaft 18 of instrument 10. Articulation rack 230 is desirably operatively associated with teeth 216 of second jaw member 204. Preferably, articulation rack 230 includes a pair of spaced apart fingers 232a, 232b extending distally therefrom. As will be described in greater detail below, fingers 232a, 232b are spaced apart an amount sufficient to allow a knife assembly 270 to be selectively reciprocated therebetween.

Each finger 232a, 232b includes at least one, preferably a plurality of, inter-engaging members 234, e.g., gears or teeth, formed thereon. Teeth 234 of articulation rack 230 are configured and dimensioned to inter-engage with and/or complement engaging elements 216 of flanges 212, 214 of second jaw member 204. In this manner, and as will be described in greater detail below, as articulation rack 230 is selectively actuated in a distal direction relative to shaft 18, second jaw member 204, and, in turn, first jaw member 202, is pivoted about the "Z" axis (i.e., about pivot pin 220) from at least an axially-aligned position to any number of articulated and/or angular positions. Likewise, as articulation rack 230 is selectively actuated in a proximal direction relative to shaft 18, second jaw member 204, and, in turn, first jaw member 202, is pivoted about the "Z" axis from the articulated and/or angular position toward a more axially-aligned position. Stated differently, fingers 232a, 232b of articulation rack 230 act as the rack of a rack and pinion type linkage while flanges 212, 214 of second jaw member 204 act as the pinion of the rack and pinion type linkage. Rack 230 is connected to an articulation control knob (not shown), which has gears in engagement with teeth on the proximal end of rack 230, so that turning of the knob axially translates the rack, pivoting the second jaw member 204.

As seen in FIGS. 12, 13 and 15-18, end effector 200 further includes a jaw actuation assembly 240 configured and adapted to permit selective movement of the first jaw member 202 relative to second jaw member 204. More particularly, actuation assembly 240 includes a resilient band 242 which extends at least substantially axially through shaft 18 and a guide 244 (see FIG. 17) which facilitates actuation of band 242. Actuation assembly 240 further includes a holder assembly 246 including a pair of spaced-apart flanges 246a, 246b. Preferably, guide 244 is rotatingly supported by flanges 246a, 246b. A supporting surface 244a of guide 244 is preferably spaced a distance "D" from the central longitudinal "X" axis of shaft 18. (see FIG. 17) The size of distance "D" determines the degree first jaw member 202 pivots relative to second jaw member 204. For example, the smaller distance "D" is, the smaller the degree of pivot of first jaw member 202 relative to second jaw member 204. Likewise, the greater distance "D" is, the greater the degree of pivot of second jaw member 204.

Figure 17:
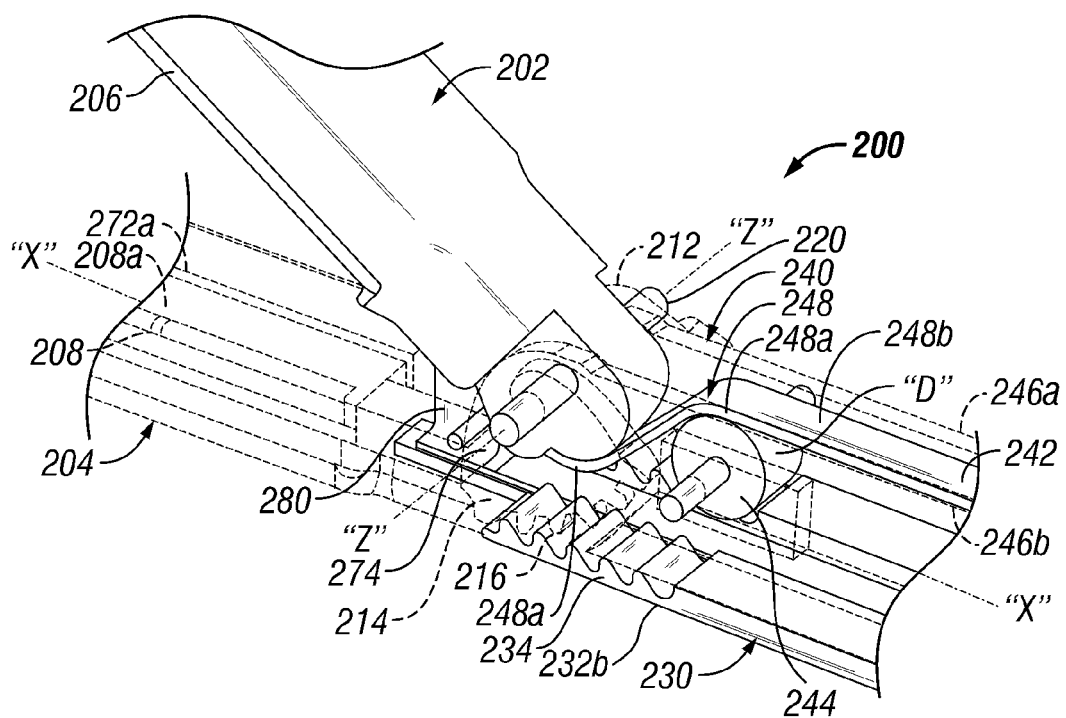
FIG. 17 is an enlarged, rear perspective view of the end effector of FIGS. 10-16, showing an axle holder shown in phantom.

Band 242 is reciprocatingly-disposed between flanges 246a, 246b of holder assembly 246. As seen in FIG. 17, band 242 includes a "gooseneck-like" distal end portion 248 having a distal end 248a fixedly secured to knuckle 218 of first jaw member 202 and a proximal end 248b extending over guide 244. The proximal end 248b is connected to a movable handle (not shown) for actuating band 242 and jaws 202, 204.

In this manner, as will be described in greater detail below, as band 242 is selectively displaced and/or advanced in a distal direction, first jaw member 202 is pivoted about the "Z" axis (and about pivot pin 220) to space first jaw member 202 from second jaw member 204 for manipulating. Additionally, as band 242 is selectively displaced in a proximal direction, first jaw member 202 is pivoted about the "Z" axis and pivot pin 220 to approximate first jaw member 202 toward second jaw member 204 for grasping tissue.

Resilient band 242 is fabricated from a material which is sufficiently pliable to be conformable to a number of arcuate and/or wave-like configurations and which is sufficiently strong enough to withstand the various axial forces associated with repeatedly grasping and manipulating tissue. Preferably, resilient band 242 is fabricated from spring steel or the like.

End effector 200 is pivotably supported between tubular extensions 250a, 250b defined at the distal end of an outer tube 250 of shaft 18. Pivot pin 220 is operatively engaged with tubular extensions 250a, 250b. Preferably, the ends of pivot pin 220 extend through and are supported by tubular extensions 250a, 250b. Tubular extensions 250a, 250b are preferably configured and dimensioned to enable end effector 200 to be pivoted from about 0° to at least about 60° relative to longitudinal axis "X" of shaft 18.

With reference to FIGS. 10-18, the present disclosure also relates a method of sealing or fusing tissue. Initially, with first and second jaw members 202, 204 of end effector 200 in a substantially axially aligned orientation or condition, end effector 200 of surgical instrument 10 may be introduced into an operative site, e.g., the thoracic cavity, through a port or the like (not shown).

Once introduced into the operative site, articulation rack 230 is actuated and/or displaced in a distal direction, as indicated by arrow "A" of FIG. 11, relative to outer tube 250. In so doing, teeth 234 of articulation rack 230 inter-engage with teeth 216 of flanges 212, 214 of second jaw member 204. As such, first and second jaw members 202, 204 are manipulated and/or rotated from the axially aligned orientation (i.e., a first position or condition) to an articulated, angular or inclined orientation (i.e., second position or condition) in which first and second jaws 202, 204 are inclined at a desired and/or necessary angle relative to longitudinal axis "X" of shaft 18.

It is envisioned that first and second jaw members 202, 204 may be displaced in about 10° angular increments. This may be accomplished with a ratchet-like mechanism (not shown). For example, a resilient pawl may be arranged in outer tube 250 for allowing the jaws 202, 204 to articulate while preventing movement in an opposite direction. The resilient pawl is desirably releasable so the jaw members can resume an axially-aligned position. The pawl may be actuated at the handle using any known means. In a further example, a mechanism or the like may be used to prevent movement after articulating the jaws to the desired position. The ratchet-like mechanism may be configured and adapted to provide sensory feedback relating to the position of end effector 200. For example, the ratchet-like mechanism may produce a "clicking" sound or other tactile or visual feedback for each 10° angular incremental displacement of end effector 200.

As jaw members 202 and 204 are pivoted about the "Z" axis and pivot pin 220, band 242 flexes and/or bends accordingly. With first and second jaw members 202, 204 in the open condition, band 242 is advanced in a distal direction, as indicated by arrow "A" of FIG. 17, to further rotate first jaw member 202, about the "Z" axis, relative to second jaw member 204 to thereby open end effector 200. In one embodiment, band 242 may be formed from any flexible and/or resilient material including metals or polymers, and laminates of metal layers, such as steel. Another possible material is a laminate of polymer and steel layers. Laminate materials allow the band to wrap around sharp radii.

With end effector 200 in the open condition, end effector 200 may be positioned within the operative site in such a manner so as to position first and second jaw members 202, 204 on opposite sides of the tissue to be treated. With end effector 200 so positioned, band 242 may be selectively drawn in a proximal direction (i.e., opposite to the direction indicated by arrow "A") in order to approximate first jaw member 202 toward second jaw member 204 and close end effector 200 about the tissue to be treated.

RF energy may then be transmitted to electrodes 206, 208 of the first and second jaw members 202, 204, respectively, to seal or fuse, the tissue. Following sealing, band 242 is again selectively driven in a distal direction to open and/or otherwise space first jaw member 202 from second jaw member 204 to release the tissue. If desired and/or necessary, the process may be repeated for new untreated tissue. The process may be repeated as many times as necessary depending upon a particular surgical purpose.

Alternatively, when desired and/or when the surgical procedure is completed, first and second jaw members 202, 204 may be returned to the axially aligned orientation by withdrawing articulation rack 230 in a direction opposite to the direction indicated by arrow "A". With first and second jaw members 202, 204 in the axially aligned orientation, end effector 200 may be withdrawn from the operative cavity.

Electrosurgical tissue fusion of lung parenchyma typically produces a seal quality which reduces the tendency of air leaks and the like, as compared to conventional surgical stapling apparatuses.

Figure 18:
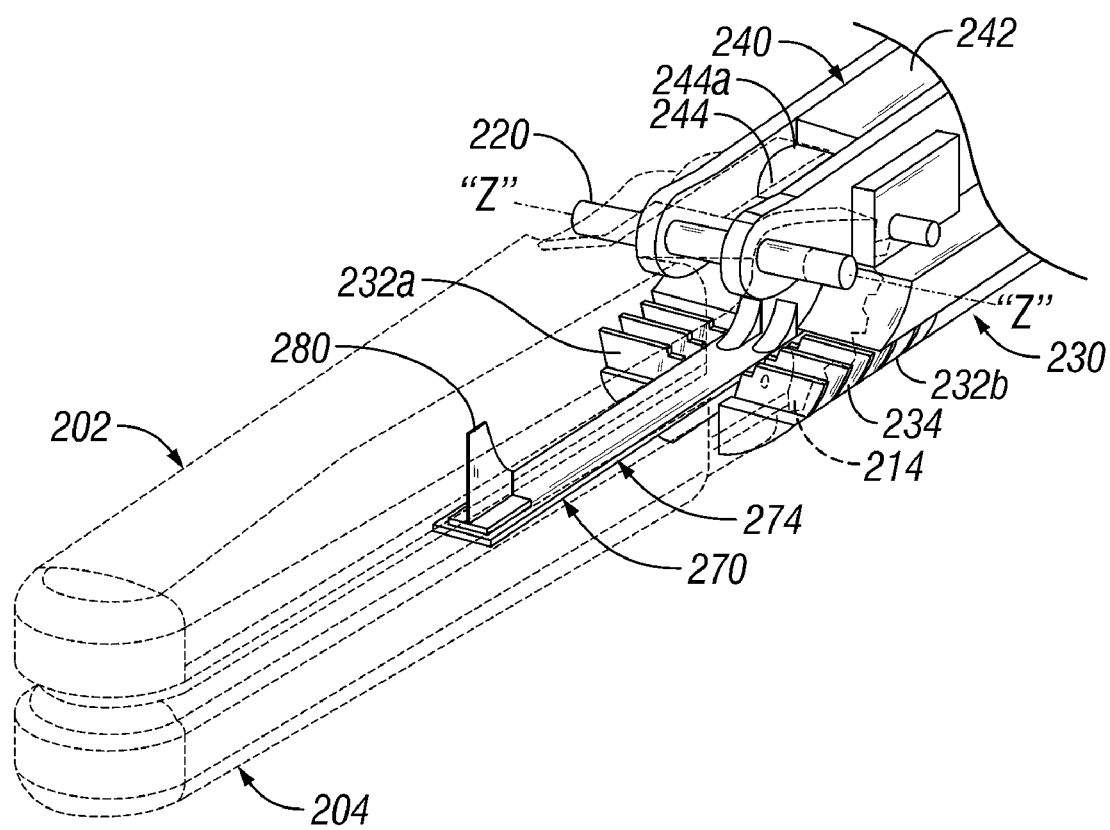
FIG. 18 is an enlarged, front perspective view of the end effector of FIGS. 10-17, with the jaw members shown in phantom, illustrating a knife carrier according to the present disclosure.

With particular reference to FIG. 18, one of first and second jaw members 202, 204, preferably second jaw member 204, is provided with a reciprocating knife assembly 270 operatively associated therewith. As seen in FIGS. 12 and 14-16, second jaw member 204 defines a longitudinally oriented knife track 272a formed in tissue contacting surface 208a of electrode 208, which extends proximally beyond tissue contacting surface 208a of second jaw member 204.

Knife assembly 270 includes a carrier 274 slidably disposed between fingers 232a, 232b of articulation rack 230. Carrier 274 is preferably fabricated from a flexible, pliable and/or resilient material such that carrier 274 may flex and/or bend with the articulation of first and second jaw members 202, 204. The carrier 274 is connected to a cutter actuation control, such as a button, knob, slider actuator or handle at the proximal end of the instrument. Carrier 274 has a perpendicular portion that is bent or otherwise formed on carrier 274 and blade 280 is welded or adhered to the perpendicular portion. Carrier 274 is preferably formed from spring metal, although polymers or other metals may be used. Knife assembly 270 further includes a knife blade 280 extending from carrier 274 and through knife track 272a.

Preferably, the first jaw member 202 is also provided with a longitudinally oriented knife track (not shown) formed in tissue contacting surface 206a of electrode 206. The knife track of first jaw member 202 is preferably disposed in vertical registration with knife track 272a of second jaw member 204 when first jaw member 202 and second jaw member 204 are in a closed orientation. In this manner, knife blade 280 is also at least partially received and/or disposed in the knife track of first jaw member 202. In addition, as carrier 274 is displaced along second jaw member 204, knife blade 280 is displaced through knife track 272a and through the knife track of first jaw member 202.

In operation and with carrier 274 in a proximal-most position in the proximal-most end of knife track 272a, first and second jaw members 202, 204 may be selectively opened and closed about tissue, as described above. Subsequent to the application of RF energy, carrier 274 may be actuated and/or driven in a distal direction thereby driving knife blade 280 through knife track 272a of second jaw member 204 and the knife track of first jaw member 202 in order to sever the effected tissue. Knife carrier 274 may also be actuated to cut tissue prior to electrosurgical activation depending upon a particular purpose.

Preferably, carrier 274 is driven in a distal direction until knife blade 280 traverses the entire length of knife track 272a or at least until knife blade 280 traverses the width of the effected tissue. Following the actuation of carrier 274 along knife track 272a (and the knife track of first jaw member 202), knife blade 280 may be returned to the proximal-most position by withdrawing carrier 274 in the proximal direction. A spring (or the like) may be employed to automatically bias the knife in the proximal-most position.

Use of knife assembly 270 to sever, divide and/or otherwise separate the tissue, following the application of RF energy, is left to the discretion of the surgeon.

Figure 19:
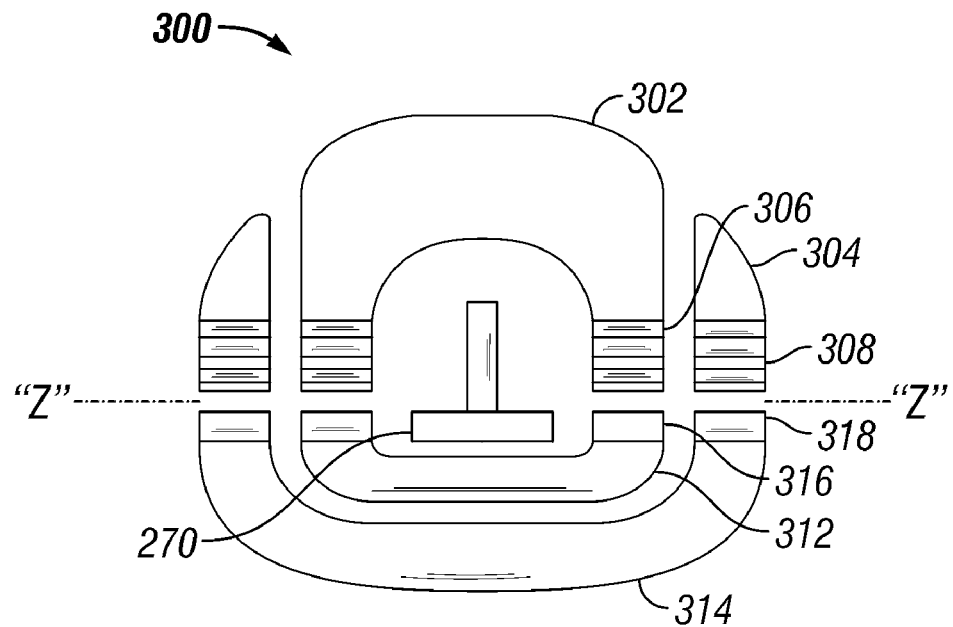
FIG. 19 is an enlarged, transverse, schematic cross-sectional view of an end effector according to another embodiment of the present disclosure, as taken through a pivot axis thereof.

Turning now to FIG. 19, which shows a schematic, transverse cross-sectional view of an alternative embodiment of an end effector 300, taken through the "Z" axis. As seen in FIG. 19, first and second jaw members 302, 304, respectively, are pivotable about a common pivot axis identified as axis "Z". A first jaw rack 312 is provided including a pair of spaced apart inter-engaging elements, e.g., gears or teeth, 316 for engaging complementary inter-engaging elements, e.g., gears or teeth, 306 provided on first jaw member 302. In this manner, as first jaw rack 312 is displaced in an axial direction relative to first jaw member 302, first jaw member 302 is pivoted about the "Z" axis. A second jaw rack 314 is provided which includes a pair of spaced apart inter-engaging elements, e.g., gear or teeth, 318 for engaging complementary inter-engaging elements, e.g., gear or teeth, 308 provided on second jaw member 304. In this manner, as second jaw rack 314 is displaced in an axial direction relative to second jaw member 304, second jaw member 304 is also pivoted about the "Z" axis. First rack 312 and second rack 314 are actuated at the proximal end of the instrument. For example, first jaw rack 312 is connected to the handle of the instrument and second jaw rack 314 is connected to a separate articulation control, such as a knob, slider or lever. Other actuators may also be used.

First jaw member 302 and second jaw member 304 are each independently pivotable about the "Z" axis relative to one another. Preferably, second jaw rack 314 is externally disposed relative to first jaw rack 312.

Figure 20:
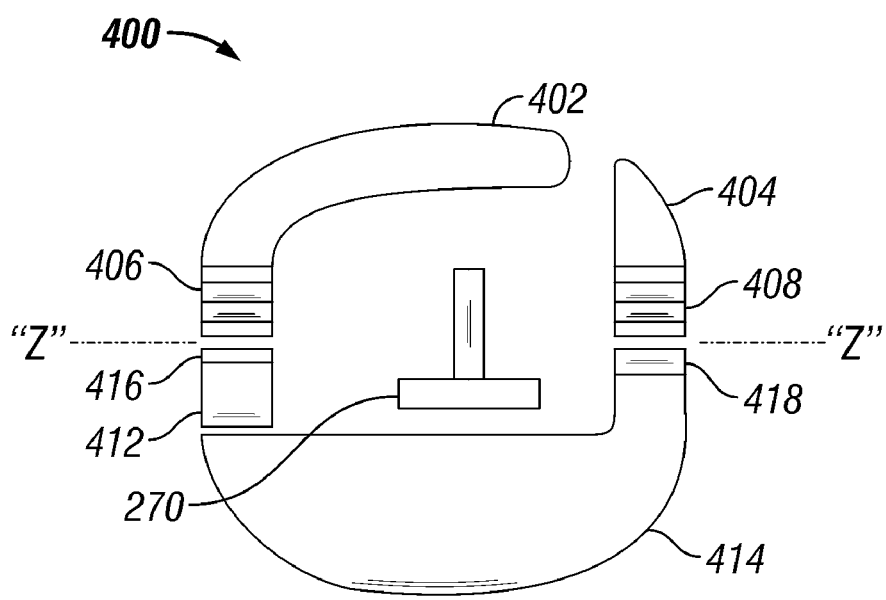
FIG. 20 is an enlarged, transverse schematic cross-sectional view of an end effector according to yet another embodiment of the present disclosure, as taken through a pivot axis thereof.
Figure 21:
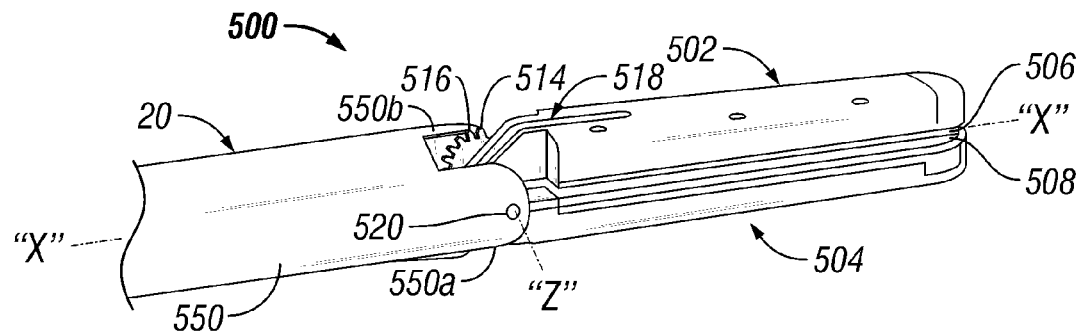
FIG. 21 is an enlarged, right side perspective view of a distal end of the surgical instrument of FIG. 1, including an end effector, in accordance with yet another embodiment of the present disclosure, showing a pair of opposed jaw members, in an axially aligned orientation.

Turning now to FIG. 20, which shows a schematic, transverse cross-sectional view of another embodiment of an end effector 400, taken through the "Z" axis. As seen in FIG. 20, first and second jaw members 402, 404, respectively, are pivotable about a common pivot axis identified as "Z". A first jaw rack 412 is provided and includes a single set of inter-engaging elements, e.g., gears or teeth, 416 for engaging a complementary set of inter-engaging elements, e.g., gears or teeth, 406 provided on first jaw member 402. In this manner, as first jaw rack 412 is displaced in an axial direction relative to first jaw member 402, first jaw member 402 pivots about the "Z" axis. A second jaw rack 414 is provided and includes a single set of inter-engaging elements, e.g., gears or teeth, 418 for engaging a complementary set of inter-engaging elements, e.g., gears or teeth, 408 provided on second jaw member 404. In this manner, as second jaw rack 414 is displaced in an axial direction relative to second jaw member 404, second jaw member 404 also pivots about the "Z" axis.

Preferably, first jaw rack 412 is disposed along a first side of jaw members 402, 404 and second jaw rack 414 is disposed along a second side of jaw members 402, 404, opposite first rack 412.

Knife assembly 270 may be provided between the first and second jaw members of each of end effectors 300, 400.

Turning now to FIGS. 21-31, an end effector in accordance with another alternate embodiment of the present disclosure is generally designated as 500. End effector 500 is similar to end effectors 100 and 200 and will only be discussed in detail to the extent necessary to identify differences in construction and operation. End effector 500 includes a first or upper jaw member 502 and a second or lower jaw member 504 pivotably associated with one another and pivotably associated with distal end 20 of shaft 18. Each jaw member 502, 504 includes a respective electrode 506, 508 in juxtaposed relation to one another. Each electrode 506, 508 defines a respective tissue contacting surface 506a, 508a (see FIG. 27).

Figure 23:
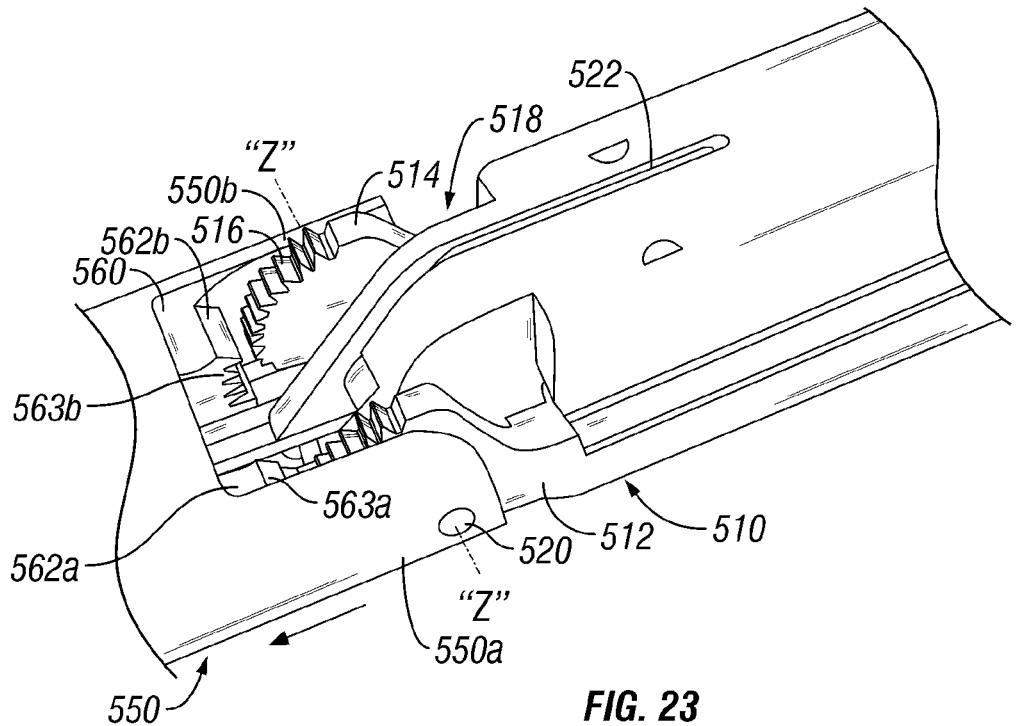
FIG. 23 is an enlarged, right side perspective view of the end effector of FIGS. 21 and 22, illustrating the jaw members in an open condition.
Figure 24:
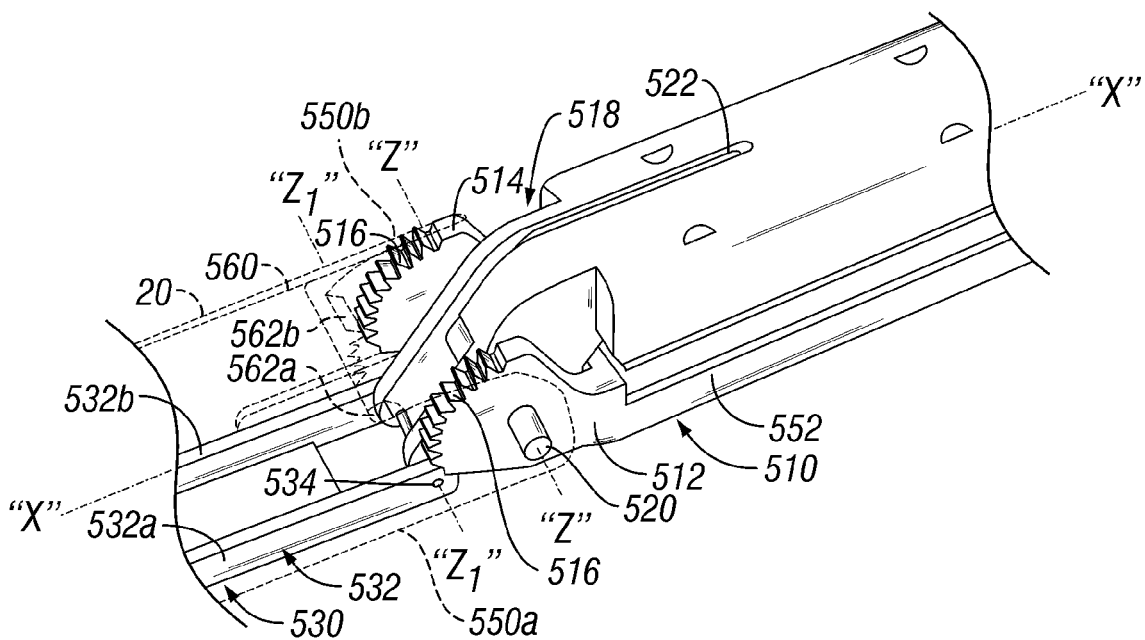
FIG. 24 is an enlarged, right side perspective view of the end effector of FIGS. 21-23, illustrating the jaw members in a closed condition.

As best seen in FIGS. 23 and 24, the proximal end of second jaw member 504 includes a yoke 510 defined by a pair of opposed spaced apart flanges 512, 514 extending therefrom. Preferably, flanges 512, 514 are at least substantially orthogonally oriented with respect to a plane defined by tissue contacting surface 508a and at least substantially parallel to longitudinal axis "X" of shaft 18. Flange 512, 514 each terminate in a proximal arcuate edge including at least one, preferably a plurality of, inter-engagement elements 516, such as, for example, teeth and the like.

First jaw member 502 includes a knuckle 518 extending from a proximal end thereof. Knuckle 518 is configured and dimensioned to be positionable between flanges 512, 514. First jaw member 502 and second jaw member 504 are pivotably connected to one another by a pivot pin 520 extending through flanges 512, 514 and knuckle 518. Pivot pin 520 defines a pivot axis "Z" which is oriented in a direction at least substantially orthogonal to longitudinal axis "X" of shaft 18 and is in a plane which is at least substantially parallel to the plane defined by tissue contacting surface 508a. Preferably, pivot pin 520 extends through longitudinal axis "X" of shaft 18.

A biasing member 522, e.g., a torsion spring, is operatively associated with first jaw member 502 and second jaw member 504. Preferably, biasing member 522 tends to bias first jaw member 502 and second jaw member 504 towards one another and tend to maintain end effector 500 closed.

Figure 22:
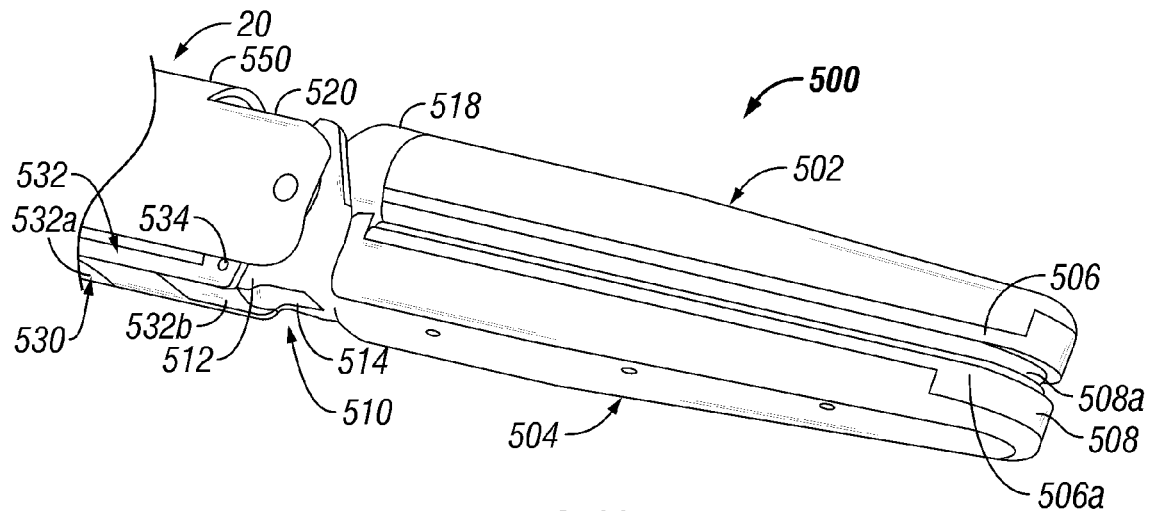
FIG. 22 is an enlarged, right side, perspective view of the end effector of FIG. 21, in an first articulated condition, showing an outer tube shown in phantom to illustrate the internal articulation joint.

As best seen in FIGS. 22 and 24, an actuation arm 530 is provided which extends through and is slidably associated with shaft 18 of instrument 10. Actuation arm 530 is desirably operatively connected to knuckle 518 of first jaw member 502. Preferably, actuation arm 530 includes a yoke 532 defined by a pair of opposed spaced apart fingers 532a, 532b extending distally therefrom. Fingers 532a, 532b are spaced apart an amount sufficient for knuckle 518 to be positioned therebetween.

Actuation arm 530 is pivotably connected to knuckle 518 by a pivot pin 534 extending through fingers 532a, 532b and through knuckle 518. Preferably, pivot pin 534 defines a pivot axis "Z1" which is substantially parallel to pivot axis "Z" of pivot pin 520. Pivot pin 534 is offset and/or spaced from pivot pin 520 in a direction away from longitudinal axis "X" of shaft 18. In use, as will be described in greater detail below, as actuation arm 530 is displaced in a distal or proximal direction, end effector 510 is caused to be pivoted about pivot pin 520, in a direction orthogonal to a plane defined by longitudinal axis "X" of shaft 18 and the pivot axis of pivot pin 520, thereby angling end effector 500 with respect to longitudinal axis "X" of shaft 18.

End effector 500 is pivotably supported between a pair of spaced apart arms 550a, 550b extending distally from an outer tube 550 of shaft 18. Pivot pin 520 is operatively engaged with arms 550a, 550b. Preferably, pivot pin 520 extends into and/or through openings 552 formed in arms 550a, 550b. Arms 550a, 550b are configured and dimensioned to enable end effector 500 to be pivoted from about 0° to at least about 60° relative to longitudinal axis "X" of shaft 18.

An inner tube 560 is slidably disposed within outer tube 550 of shaft 18. Inner tube 560 includes at least one, preferably a pair of, engagement members 562a, 562b, configured and dimensioned to selectively engage with inter-engagement elements 516 of flanges 512, 514 of second jaw member 504. Each engagement member 562a, 562b includes a plurality of teeth providing improved meshing characteristics with engagement elements 516 of flanges 512, 514. In addition, the increased number of teeth tends to better distribute the load and/or forces over the entire length of engagement elements 516 of flanges 512, 514 and engagement members 562a, 562b of inner tube 560.

Preferably, inner tube 560 includes a yoke 564 defined by a pair of opposed spaced apart plate members 564a, 564b extending distally therefrom. Plate members 564a, 564b are spaced apart an amount sufficient for flanges 512, 514 of second jaw member 504 and knuckle 518 of first jaw member 502 to be positioned therebetween. Each plate member 564a, 564b includes a slot 566 formed therein. Preferably, slots 566 are longitudinally oriented and in registration with openings 552 formed in arms 550a, 550b of outer tube 550. Pivot pin 520 preferably extends through slots 566.

Outer tube 550 and inner tube 560 have a first position in which outer tube 550 is in a distal-most position relative to inner tube 560. When outer tube 550 is in the distal-most position, pivot pin 520 is positioned in the distal end of slots 566 and engagement members 562a, 562b of inner tube 560 are disengaged from inter-engagement elements 516 of flanges 512, 514. In addition, when outer tube 550 is in the distal-most position, end effector 500 is capable of being pivoted about pivot pin 520.

Outer tube 550 and inner tube 560 have a second position in which outer tube 550 is in a proximal-most position relative to inner tube 560. When outer tube 550 is in the proximal-most position, pivot pin 520 is positioned in the proximal end of slots 566 and engagement members 562a, 562b of inner tube 560 are engaged with inter-engagement elements 516 of flanges 512, 514. In this manner, when outer tube 550 is in the proximal-most position, end effector 500 is locked in position relative to shaft 18.

With reference to FIGS. 21-29, a method of operation and/or of using end effector 500 will be shown and described. Initially, with first and second jaw members 502, 504 of end effector 500 in a substantially aligned orientation and with outer tube 550 in the proximal-most position, end effector 500 can be introduced into an operative site, e.g., the thoracic cavity, through a thoroscopic port or the like.

Figure 25:
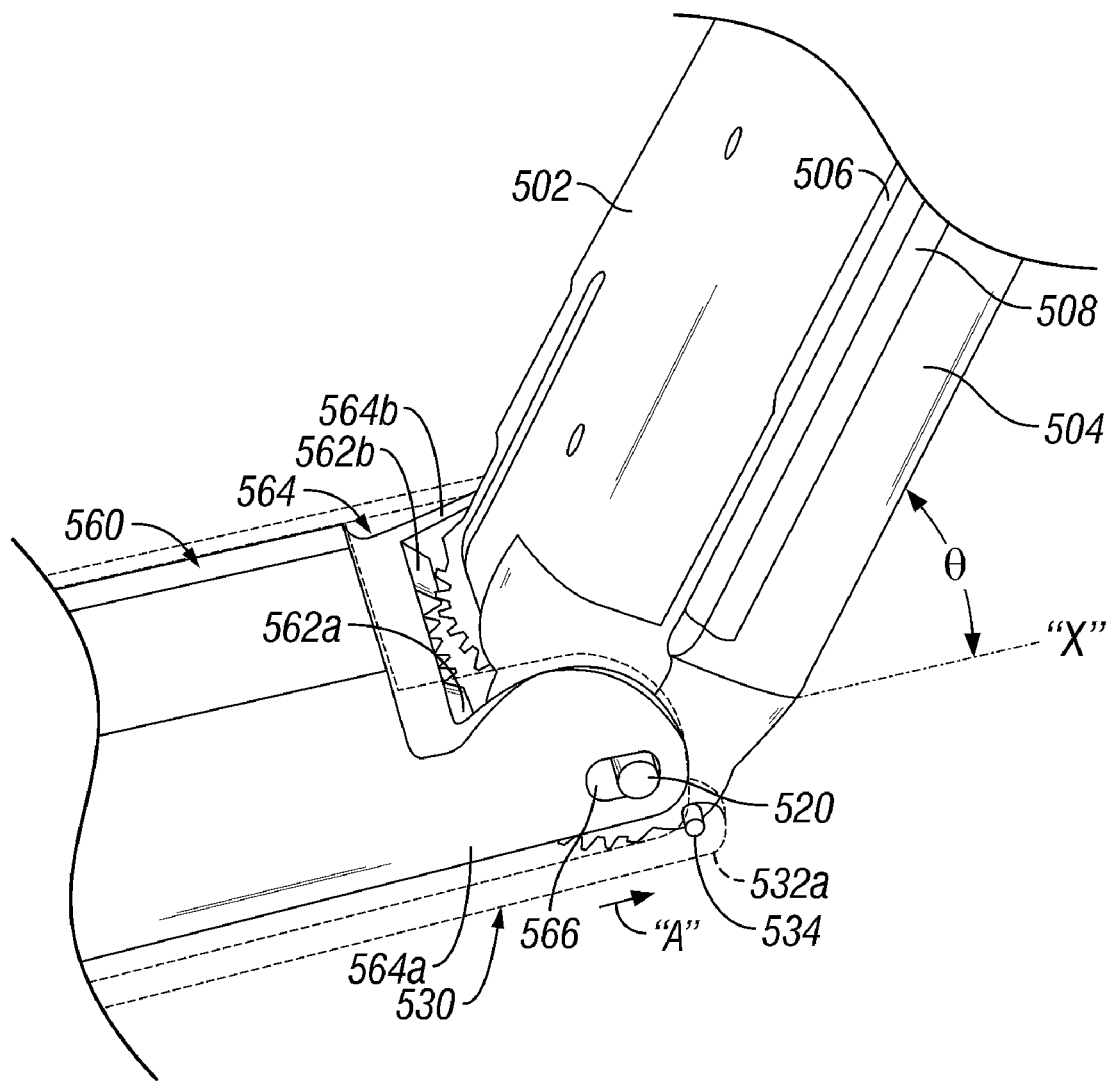
FIG. 25 is an enlarged, front perspective view of the end effector of FIGS. 21-24 showing the jaw members in the axially aligned orientation and with the jaws in the open condition.
Figure 26:
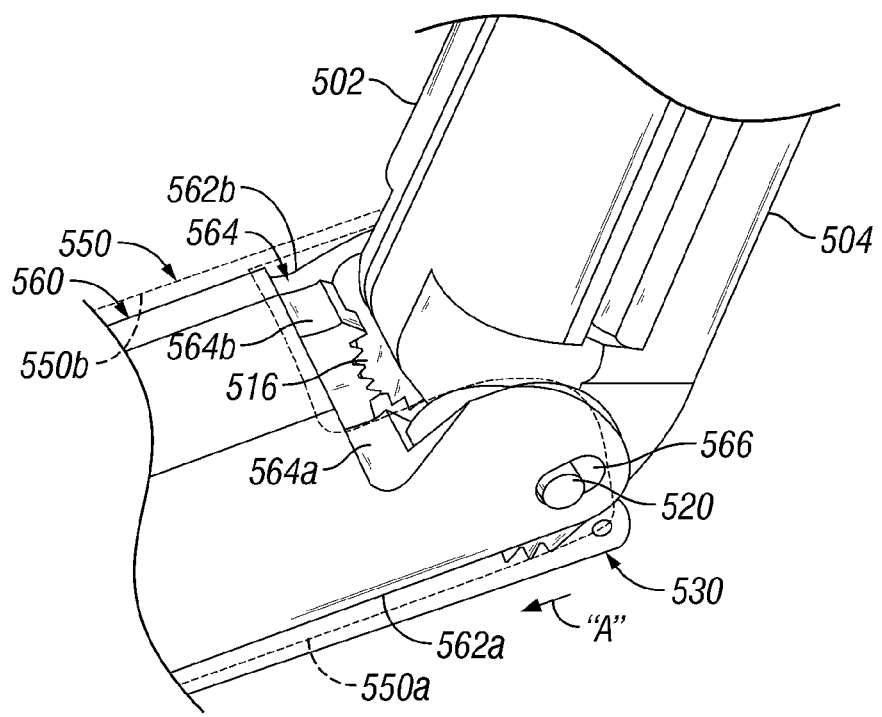
FIG. 26 is an enlarged, right side perspective view of the end effector of FIGS. 21-25, in a second articulated condition, with the outer tube shown in phantom.
Figure 27:
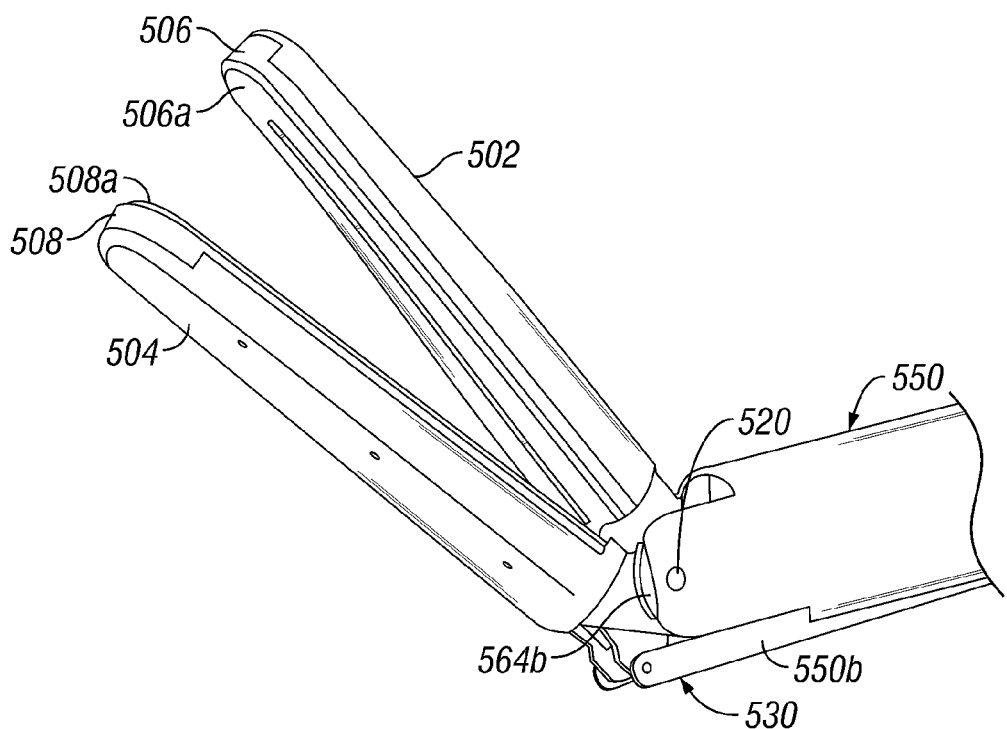
FIG. 27 is an enlarged, top perspective view of the end effector of FIGS. 21-26.
Figure 28:
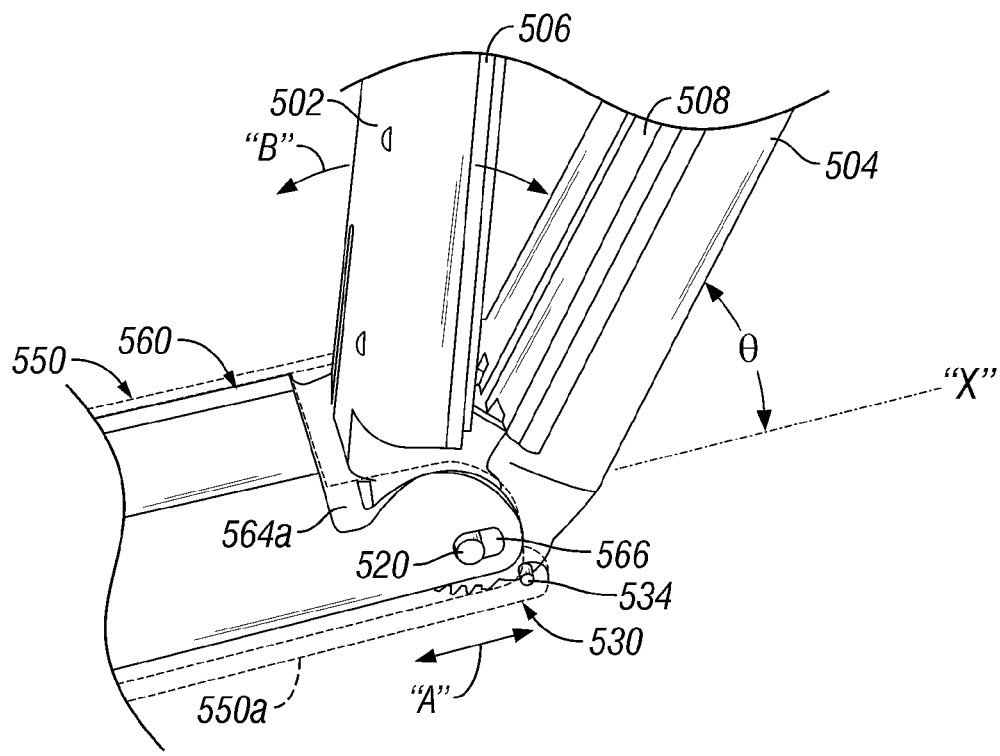
FIG. 28 is an enlarged, rear perspective view of the end effector of FIGS. 21-27, showing an axle holder shown in phantom.
Figure 29:
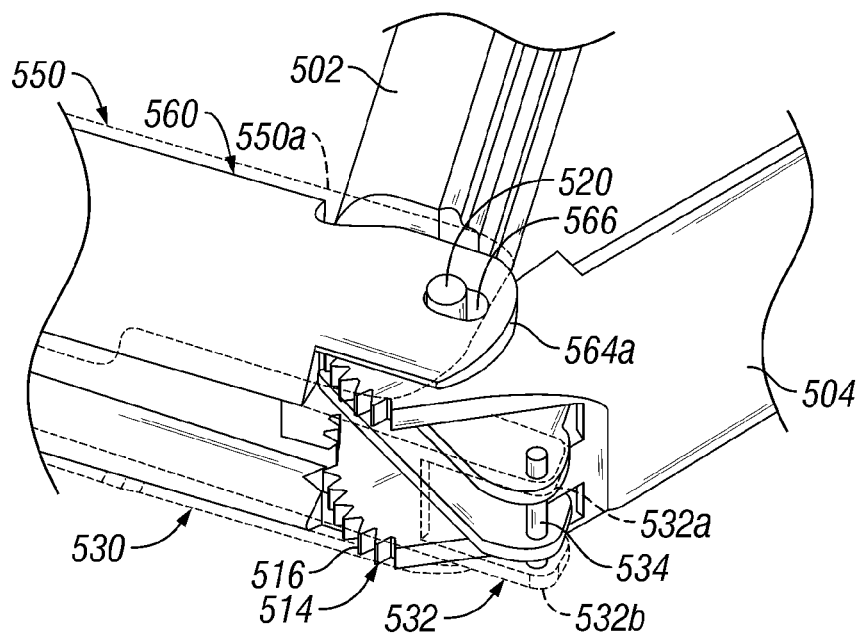
FIG. 29 is an enlarged, front perspective view of the end effector of FIGS. 21-28, with the jaw members shown in phantom, illustrating a knife carrier according to the present disclosure.

Once introduced into the operative site, actuation arm 530 is actuated and/or displaced in a distal direction, as indicated by arrow "A" of FIG. 25, relative to shaft 18. In so doing, actuation arm 530 drives pivot pin 534 in a distal direction thereby causing first jaw 502 to pivot about axis "Z" of pivot pin 520, as indicated by arrow "B" of FIG. 25. With outer tube 550 in a distal-most position relative to inner tube 560, second jaw 504 is free to be urged through the biasing member about axis "Z" of pivot pin 520. With outer tube 550 in a proximal-most position relative to inner tube 560, second jaw 504 is engaged by inter-engagement element 516 and will remain in place while first jaw 502 pivots about pivot pin 520. Inter-engagement elements 516 allow for a plurality of angular inclinations "⊖", of second jaw 504, from about 0° to about 60°, relative to longitudinal axis "X" of shaft 18.

Biasing member 522 has a spring constant "K" selected such that biasing member 522 tends to maintain end effector 500 in a closed condition (i.e., first jaw member 502 and second jaw member 504 at least substantially approximated toward one another) during manipulation of end effector 500 from the axially aligned orientation to the angularly inclined orientation.

It is envisioned that end effector 500 may be displaced in about 10° angular increments by using articulation knob 150 as described above with regard to FIGS. 1-9. It is envisioned that surgical instrument 10 may be provided with sensory feedback which indicates to the user the orientation or condition of end effector 500. For example, surgical instrument 10 may produce a "clicking" sound or other tactile feedback for each 10° angular incremental displacement of end effector 500.

With end effector 500 in the second condition (i.e., in the desired and/or necessary angular inclination "⊖"), outer tube 550 is displaced in a proximal direction relative to inner tube 560 to thereby inter-engage engagement members 562a, 562b of inner tube 560 with inter-engagement elements 516 of end effector 500. In so doing, pivot pin 520 is displaced from the distal-most position in slots 566 to the proximal-most position in slots 566. As such, end effector 500 is effectively locked in the second condition and prevented from returning to the first condition (i.e., the axially aligned condition).

With end effector 500 locked in the second condition, end effector 500 is caused to be opened by once again driving actuation arm 530 in a distal direction with a force sufficient to overcome the force of spring constant "K" of biasing member 522. In so doing, first jaw member 502 is caused to be pivoted about axis "Z" of pivot pin 520, e.g., actuation arm 530 presses into pivot pin 532 thereby urging first jaw member 502 to pivot about pivot pin 520 and space first jaw member 502 from second jaw member 504.

With end effector 500 in an opened condition, end effector 500 can be positioned within the operative site in such a manner so as to position jaw members 502, 504 on opposite sides of tissue to be effected. With end effector 500 so positioned, the force on actuation arm 530 can be removed or actuation arm 530 can be withdrawn in a proximal direction to thereby close end effector 500 (i.e., approximate first jaw member 502 toward second jaw member 504) on to the tissue. RF energy can then be transmitted to electrodes 506, 508 of jaw members 502, 504, respectively, to fuse, cauterize, seal and/or otherwise electrosurgically affect the tissue.

Following RF treatment of the tissue, actuation arm 530 is driven in a distal direction to once again open end effector 500. If desired and/or necessary, end effector 500 is disassociated from the affected tissue and positioned around new unaffected tissue and the process repeated. The process is repeated as many times as necessary to complete the surgical procedure and/or as many times as desired.

Alternatively, when desired and/or when the surgical procedure is completed, outer tube 550 is urged in a distal direction to disassociate inter-engagement elements 516 of flanges 512, 514 from engagement members 562a, 562b of inner tube 560. Actuation arm 530 can then be withdrawn in a proximal direction to return end effector 500 to the first or substantially axially aligned orientation with longitudinal axis "X" of shaft 18. With end effector 500 so positioned, end effector 500 can be withdrawn from the thoracic cavity.

With reference to FIGS. 30 and 31, one of jaw members 502, 504, preferably second jaw member 504 is provided with reciprocating knife assembly 570 operatively associated therewith. Second jaw member 504 defines a longitudinally oriented knife track 572 formed in tissue contacting surface 508a of electrode 508. Knife assembly 570 includes a cable loop 574 extending substantially along knife track 572 and wrapping around a spindle or turnaround 576. Cable loop 574 defines a first portion 574a and a second portion 574b. Operatively, first portion 574a or second portion 574b is fixedly secured to carrier member 578. For purposes of this disclosure, it is assumed that first portion of cable 574a is fixedly secured to carrier member 578.

Knife assembly 570 further includes a knife blade carrier member 578 slidably disposed within second jaw member 504 and operatively associated with cable loop 574. Knife assembly 570 further includes a knife blade 580 extending from carrier member 578 and extending through knife track 572.

Preferably, first jaw member 502 is also provided with a longitudinally oriented knife track (not shown) formed in tissue contacting surface 506a of electrode 506. The knife track of first jaw member 502 is preferably in registration with knife track 572 of second jaw member 504 when first jaw member 502 and second jaw member 504 are in approximation with one another. In this manner, when first jaw member 502 and second jaw member 504 are in approximation with one another, knife blade is also at least partially received in the knife track of first jaw member 502. In addition, as carrier member 578 is displaced along second jaw member 504, knife blade 580 is displaced through knife track 572 and through the knife track of first jaw member 502.

In operation, with carrier member 578 at a proximal-most position along the length of knife track 572, as first portion 574a of cable loop 574 is drawn in a proximal direction, second portion 574b of cable loop 574 is drawn around spindle 576 thereby causing carrier member 578, and in turn knife blade 580, to be pulled in a distal direction along knife track 572. Following actuation of carrier member 578 along knife track 572, carrier member 578 is returned to the proximal-most position by withdrawing second portion 574b of cable loop 574 in a proximal direction.

If desired, knife assembly 570 may be used in the procedure described above to sever, divide and/or otherwise separate the tissue following the application of RF energy thereto.

Preferably, cable loop 574 is fabricated from a flexible material thereby enabling carrier member 578 to be driven in a distal or proximal direction while end effector 500 is at any angular inclination "Θ" relative to longitudinal axis "X" of shaft 18.

From the foregoing and with reference to the various figure drawings, those skilled in the art will appreciate that certain modifications may also be made to the present disclosure without departing from the scope of the present disclosure.

For example, one or more stop members may be employed to regulate the gap distance between the opposing sealing or tissue contacting surfaces 106a, 108a to optimize sealing. For example, as described in commonly-owned U.S. application Ser. Nos. 10/116,944, filed on Apr. 5, 2002; 10/179,863, filed on Jun. 25, 2002; 10/472,295, filed on Sep. 18, 2003; 10/474, 169, filed on Oct. 3, 2003; and International Application No. PCT/US02/01890, filed on Jan. 22, 2002, each entitled "Vessel Sealer and Divider"; and U.S. application Ser. No. 10/369, 894, filed on Feb. 20, 2003, entitled "Vessel Sealer and Divider and Method for Making Same", the entire disclosure of each of which being incorporated herein by reference, one or more stop members may be positioned on one or both sealing surfaces to regulate the gap distance to between about 0.001 inches to about 0.006 inches for sealing tissue which is about 1 mm in diameter or thickness to about 11 mm in diameter or thickness. For larger tissue, it is envisioned that providing stop members which regulate the gap distance from about 0.002 inches to about 0.009 inches is desirable to optimize sealing. For a tissue sealing device optimized for lung applications, a gap distance of about 0.005 inches may be used.

It is also envisioned that articulation knob 150, when end effector 100 is clamped on the tissue to be treated, may be rotated to provide adjustment in closure pressure, between the opposing sealing and/or tissue contacting surfaces 160a, 108a of first and second jaw members 102, 104, in the range of about 3 kg/cm$^2$ to about 16 kg/cm$^2$ and more preferably about 3.5 to about 8.5 kg/cm$^2$ to optimize sealing of larger structures such as lung and bowel tissue.

It is also envisioned that first and second jaw members 102, 104 may be configured to minimize collateral tissue damage and minimize thermal spread as disclosed in commonly-owned U.S. application Ser. Nos. 10/474,273, filed on Oct. 3, 2003, entitled "Electrosurgical Instrument Which Reduces Effect to Adjacent Tissue"; 10/388,953, filed on Jan. 1, 2003, entitled "Bi-Polar Electrosurgical Forceps with Non-Conductive Stop Member; 10/474,168, filed on Oct. 3, 2003, entitled "Electrosurgical Instrument Which Reduces Collateral Damage to Adjacent Tissue"; and 10/712,486, filed on Nov. 13, 2003, entitled "Compressible Jaw Configuration with Bipolar RF Output Electrodes for Soft Tissue Fusion", the entire contents of each of which being incorporated herein by reference.

It is further desirably, as seen in FIG. 1, that instrument 10 is provided with a reverse pivoting handle 26 for improved ergonomics and increased leverage (i.e., application of a squeezing force to handle 26 in order to actuate instrument 10). Orientation (i.e., the position and angle of rotation) of the movable handle in conventional surgical instruments are typically not naturally compatible with the human hand. For instance, rotation and/or actuation of the typical movable handle typically undergoes its greatest displacement in the area effected (i.e., the application of a squeezing force) by the smallest digit (i.e., the pinkie), meanwhile the smallest displacement of the typical moveable handle is associated with the application of a squeezing force by the index finger. As a result, many users may not be able to engage the movable handle, when in the fully un-actuated position, with their smallest digit and thus the smallest digit is unable to contribute to the squeezing and/or actuation of the movable handle.

In accordance with the present disclosure, the typical movable handle has been replaced with a reverse pivoting handle 26. In this manner, the greatest displacement of movable handle 26 takes place in the vicinity of the user's index finger while the smallest displacement of pivoting handle 26 takes place in the vicinity of the user's smallest digit. Accordingly, the smallest digit, typically the pinkie, is able to contribute to the actuation and/or squeezing of movable handle 26.

Although the present disclosure has been described with respect to particular embodiments, it will be readily apparent to those having ordinary skill in the art to which it appertains that changes and modifications may be made thereto without departing from the spirit and scope of the present disclosure.

What is claimed is:

1. A bipolar electrosurgical instrument, comprising:
   a housing;
   a handle assembly operatively associated with the housing;
   a shaft extending from the housing, the shaft defining a longitudinal axis;
   an end effector operatively associated with a distal end of the shaft, the end effector comprising:
      a first jaw member pivotably coupled to the distal end of the shaft;
      a second jaw member pivotably coupled to the distal end of the shaft and in juxtaposed relation to the first jaw member, the first and second jaw members being movable from a first orientation in which the first and the second jaw member are axially aligned with the longitudinal axis and a plurality of second orientations in which the first and second jaw members are angled with respect to the longitudinal axis, the first and second jaw members having an open condition in which the first and second jaws members are spaced from one another and a closed condition in which the first and second jaw members are substantially in close proximity to one another, the second jaw member comprising a plurality of inter-engagement elements;
   a locking mechanism operatively associated with the second jaw member, the locking mechanism comprising:
      a locking shaft extending longitudinally through the shaft, the locking shaft having a distal end operatively associated with the second jaw member and including a locking pin extending transversely from the distal end of the locking shaft, the locking pin selectively engagable with each of the plurality of inter-engagement elements of the second jaw member; and
   an actuation mechanism operatively connected to the first jaw member, the actuation mechanism comprising:
      an actuation shaft reciprocally and rotatably disposed in the locking shaft, the actuation shaft having a distal end and a proximal end; and
      a band having a proximal end operatively connected to the distal end of the actuation shaft, and a distal end extending through an aperture formed in the distal end of the locking shaft and operatively connected to the first jaw member.

2. The electrosurgical instrument according to claim 1, further comprising:
   an articulation knob operatively associated with the locking mechanism and the actuation mechanism, wherein the articulation knob effectuates independent operation of one of the locking mechanism and the actuation mechanism.

3. The electrosurgical instrument according to claim 2, wherein rotation of the articulation knob manipulates the actuation mechanism to move the first jaw member between the first orientation and the plurality of second orientations.

4. The electrosurgical instrument according to claim 2, wherein the locking mechanism comprises:
   a first collar operatively connected to a proximal end of the locking shaft;
   a pair of diametrically opposed connecting rods extending proximally from the first collar; and
   a second collar operatively connected to the proximal end of at least one of the connecting rods, the second collar being rotatably supported on the articulation knob, wherein as the articulation knob is axially displaced in one of a proximal and distal directions, the connecting rods transmit the axial displacement of the articulation knob to the locking rod.

5. The electrosurgical instrument according to claim 1, wherein the actuation mechanism further comprises:
   a lead screw operatively connected to a proximal end of the actuation shaft; and
   a drive shaft operatively interconnecting the lead screw and the articulation knob;
   wherein rotation of the articulation knob moves the drive shaft, and wherein the drive shaft transmits rotation to the lead screw, and
   wherein and the lead screw axially displaces the actuation shaft.

6. The electrosurgical instrument according to claim 4, further comprising an indexing plate operatively associated with at least one of the connecting rods, the indexing plate operatively engagable with the articulation knob, the indexing plate defining a plurality of angular orientations for the second jaw member.

7. The electrosurgical instrument according to claim 1, wherein the second jaw member is biased to the axially aligned orientation.

8. The electrosurgical instrument according to claim 1, wherein the end effector further comprises a pivot pin extending through the first and the second jaw members, the pivot pin being transversely oriented with respect to the longitudinal axis, the pivot pin being coplanar with respect to a plane defined by a tissue contacting surface of the second jaw member.

9. The electrosurgical instrument according to claim 1, wherein the band is fabricated from a material capable of transmitting compressive and tensile loads.

10. The electrosurgical instrument according to claim 1, wherein the band comprises spring steel.

11. The electrosurgical instrument according to claim 1, further comprising electrodes disposed on the first and the second jaw members, the electrodes being in juxtaposed relation to one another when the first and the second jaw members are substantially aligned.

12. The electrosurgical instrument according to claim 1, wherein the second jaw member comprises a pair of spaced apart flanges extending proximally therefrom, wherein each flange is provided with at least one inter-engaging element, and wherein the first jaw member includes a knuckle extending proximally therefrom, the knuckle being disposed between the pair of flanges.

13. The electrosurgical instrument according to claim 12, wherein the band is pivotably connected to the knuckle at a predetermined location, the predetermined location being spaced a transverse distance from the pivot pin in the longitudinal axis.

14. The electrosurgical instrument according to claim 1, wherein the handle assembly further comprises a reverse pivoting handle.

15. The electrosurgical instrument according to claim 14, further comprising a series of linkages configured and adapted to urge the lead screw in a distal direction and drive the actuation shaft in the distal direction when the pivoting handle is squeezed.

* * * * *